US011827683B2

(12) United States Patent
Temple et al.

(10) Patent No.: US 11,827,683 B2
(45) Date of Patent: *Nov. 28, 2023

(54) BI-FUNCTIONAL ANTI-TAU POLYPEPTIDES AND USE THEREOF

(71) Applicant: Regenerative Research Foundation, Rensselaer, NY (US)

(72) Inventors: Sally Temple, Rensselaer, NY (US); Anne Messer, Rensselaer, NY (US); David Butler, Rensselaer, NY (US)

(73) Assignee: Regenerative Research Foundation, Rensselaer, NY (US)

( * ) Notice: Subject to any disclaimer, the term of this patent is extended or adjusted under 35 U.S.C. 154(b) by 108 days.

This patent is subject to a terminal disclaimer.

(21) Appl. No.: 17/385,252

(22) Filed: Jul. 26, 2021

(65) Prior Publication Data

US 2022/0002365 A1 Jan. 6, 2022

Related U.S. Application Data

(63) Continuation of application No. 16/331,063, filed as application No. PCT/US2017/050764 on Sep. 8, 2017, now Pat. No. 11,072,639.

(60) Provisional application No. 62/385,019, filed on Sep. 8, 2016.

(51) Int. Cl.
*C07K 14/47* (2006.01)
*A61P 25/28* (2006.01)
*C07K 16/08* (2006.01)
*C07K 16/18* (2006.01)
*A61K 38/00* (2006.01)

(52) U.S. Cl.
CPC .......... *C07K 14/4711* (2013.01); *A61P 25/28* (2018.01); *C07K 16/18* (2013.01); *A61K 38/00* (2013.01); *C07K 2317/24* (2013.01); *C07K 2317/622* (2013.01); *C07K 2317/94* (2013.01); *C07K 2319/95* (2013.01)

(58) Field of Classification Search
CPC ................ C07K 14/4711; C07K 16/18; C07K 2317/24; C07K 2319/95; A61P 25/28
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 5,179,017 A | 1/1993 | Axel et al. |
| 5,641,640 A | 6/1997 | Hanning |
| 11,072,639 B2 | 7/2021 | Temple et al. |
| 2002/0197258 A1 | 12/2002 | Ghanbari et al. |
| 2008/0131373 A1 | 6/2008 | Cao |
| 2009/0220960 A1 | 11/2009 | Ohmiya et al. |
| 2012/0087861 A1 | 4/2012 | Nitsch et al. |
| 2013/0004493 A1 | 1/2013 | Gordon et al. |
| 2019/0202879 A1* | 7/2019 | Temple .............. C07K 14/4711 |

FOREIGN PATENT DOCUMENTS

| | | |
|---|---|---|
| WO | WO 1999054348 | 10/1999 |
| WO | WO 2003014960 | 2/2003 |
| WO | WO 2010119520 | 8/2010 |
| WO | WO 2011119523 | 8/2010 |
| WO | WO 2016007414 | 1/2016 |
| WO | WO 2016119523 | 8/2016 |

OTHER PUBLICATIONS

Rudikoff et al. Proc Natl Acad Sci USA 1982 vol. 79, p. 1979 (Year: 1982).*
Berge et al., "Pharmaceutical salts," Journal of Pharmaceutical Sciences, Jan. 1977, 66(1):1-19.
Better et al., "[33] Expression of engineered antibodies and antibody fragments in microorganisms," Methods in Enzymology, 1989, 178:476-496.
Better et al., "*Escherichia coli* secretion of an active chimeric antibody fragment," Science, May 20, 1998, 240(485):1041-1043.
Bird et al., "Single chain antibody variable regions," Apr. 1991, 9(4):132-137.
Butler et al. Bifunctional Anti-Huntingtin Proteasome-Directed Intrabodies Mediate Efficient Degradation of Mutant Huntingtin Exon 1 Protein Fragments. PloS One, 2011, vol. 6, No. 12: e29199; pp. 1-11.
Co et al., "A humanized antibody specific for the platelet integrin gpIIb/IIIa.," Journal of Immunology, Mar. 15, 1994, 152(6):2968-2976.
Ehrlich et al., "ST14A Cells Have Properties of a Medium-Size Spiny Neuron," Experimental Neurology, 2001, 167(2):215-226.
Extended European Search Report in International Appln. No. 17849650.1, dated May 20, 2020, 23 pages.
GenBank accession No. AEE36488.1, Apr. 26, 2010.
GenBank accession No. CA079114.1, July 3, 2007.
Hudson et al., "High avidity scFv multimers; diabodies and triabodies," Journal of Immunological Methods, Dec. 10, 1999, 231(1-2):177-189.
Huston et al., "Protein engineering of antibody binding sites: recovery of specific activity in an anti- digoxin single-chain Fv analogue produced in *Escherichia coli*," Proceedings of the National Academy of Sciences of the United States of America, Aug. 1988, 85:5879-5883.
Johne et al., "Epitope mapping and binding kinetics of monoclonal antibodies studied by real time biospecific interaction analysis using surface plasmon resonance," Journal of Immunological Methods, Apr. 2, 1993, 160(2):191-198.
Kaufman et al., "Amplification and expression of sequences cotransfected with a modular dihydrofolate reductase complementary DNA gene," Journal of Molecular Biology, Aug. 2, 1982, 159(4):601-621.

(Continued)

*Primary Examiner* — Kimberly Ballard
*Assistant Examiner* — Stacey N Macfarlane
(74) *Attorney, Agent, or Firm* — Fish & Richardson P.C.

(57) ABSTRACT

Disclosed herein are multifunctional polypeptides comprising a first domain comprising an anti-tau antigen binding domain and a second domain comprising a proteasome-targeting PEST motif, and methods for using these polypeptides in treatment of tauopathies.

22 Claims, 4 Drawing Sheets

Specification includes a Sequence Listing.

(56) References Cited

OTHER PUBLICATIONS

Lamoyi, "Preparation of F(ab')2 fragments from mouse IgG of various subclasses," Methods in Enzymology, 1986, 121(62):652-663.

Lei et al., "Characterization of the Erwinia carotovora pelB gene and its product pectate lyase," Journal of Bacteriology, Sep. 1987, 169(9):4379-4383.

Mizushima et al., "pEF-BOS, a powerful mammalian expression vector," Nucleic Acids Research, 1990, 18917):5322.

Mulligan et al., "Synthesis of rabbit β-globin in cultured monkey kidney cells following infection with a SV40 β-globin recombinant genome," Nature, Jan. 1, 1979, 277:108-114.

PCT International Preliminary Report on Patentability in International Application No. PCT/US2017/050764, dated Mar. 21, 2019, 12 pages.

PCT International Search Report in International Application No. PCT/US2017/050764, dated Jan. 5, 2018, 4 pages.

PCT Invitation to Pay Additional Fees in International Application No. PCT/US2017/050764, dated Nov. 2, 2017, 3 pages.

Pluckthun et al., "[34] Expression of functional antibody Fv and Fab fragments in *Escherichia coli*," Methods in Enzymology, 1989, 178:497-515.

Rousseaux et al., "Optimal conditions for the preparation of proteolytic fragments from monoclonal IgG of different rat IgG subclasses," Methods in Enzymology, 1989, 121(63):663-669.

Sjolander et al., "Integrated fluid handling system for biomolecular interaction analysis," Analytical Chemistry, Oct. 15, 1991, 63(20):2338-2345.

Szabo et al., "Surface plasmon resonance and its use in biomolecular interaction analysis (BIA)," Current Opinion in Structural Biology, Oct. 1995, 5(5):699-705.

The Pharmacology of Monoclonal Antibodies, vol. 113, Rosenburg et al. (ed)., 1994, Chapter 11: Antibodies from *Escherichia coli*, pp. 269-315.

Urlaub et al., "Isolation of Chinese hamster cell mutants deficient in dihydrofolate reductase activity," Proceedings of the National Academy of Sciences of the United States of America, Jul. 1980, 77(7):4216-4220.

Ward et al., "Binding activities of a repertoire of single immunoglobulin variable domains secreted from *Escherichia coli*," Oct. 12, 1989, 341:544-546.

Yanannandra et al. "Anti-tau antibodies that block tau aggregate seeding in vitro markedly decrease pathology and improve cognition in vivo. Neuron," 2013;80(2):402-14 (Year: 2013).

* cited by examiner

FIG. 2

BI-FUNCTIONAL ANTI-TAU POLYPEPTIDES AND USE THEREOF

CROSS-REFERENCE TO RELATED APPLICATIONS

This application is a continuation of U.S. patent application Ser. No. 16/331,063, filed Mar. 6, 2019 which is a U.S. National Phase application under 35 U.S.C. § 371 of International Patent Application No. PCT/US2017/050764 filed Sep. 8, 2017, which PCT/US2017/050764 claims the benefit of priority of U.S. Provisional Application No. 62/385,019, filed Sep. 8, 2016, the contents of which are incorporated by reference herein in their entirety.

SEQUENCE LISTING

This document includes a sequence listing submitted to the United States Patent and Trademark Office via the electronic filing system as an ASCII text file. The sequence listing, which is incorporated-by-reference herein, is titled "Sequence_listing," was created on Jun. 1, 2021, and has a size of 123 kilobytes.

TECHNICAL FIELD

This invention relates to multifunctional polypeptides comprising an anti-tau antibody or functional fragment thereof, and methods for using these polypeptides in treatment of tauopathies.

BACKGROUND

Tau is a microtubule-associated phosophoprotein expressed in the central and peripheral nervous system. Tau plays a role in many biological processes such as microtubule stabilization, neurite outgrowth, neuronal migration, signal transduction, and organelle transport. Under normal conditions, tau expression is abundant within the axons of neurons. The misfolding and aggregation of tau within neurons are defining pathological hallmarks in a variety of neurodegenerative diseases collectively known as tauopathies. Tauopathies include Alzheimer's disease (AD), Fronto-temporal Dementia with Parkinsonism on chromosome-17 (FTDP-17), Pick's disease, Corticobasal Degeneration (CBD), Progressive Supranuclear Palsy (PSP), Dementia pugilistica (chronic traumatic encephalopathy), Lytico-Bodig disease, ganglioglioma and gangliocytoma, Meningioangiomatosis, Subacute sclerosing panencephalitis, lead encephalopathy, Tuberous sclerosis, Hallervorden-Spatz disease and others. The incidence of tauopathies represent an urgent and unmet medical need.

In tauopathies, tau protein loses its ability to bind to microtubules, and as a result tau is mislocalized to the dendritic compartment of the neuron. During this process, tau is hyperphosphorylated and misfolds into insoluble aggregates of straight filaments and paired helical filaments (PHF) which comprise neurofibrillary tangles and threads (NFTs). Tau hyperphosphorylation is presumed to occur prior to NFT formation. Furthermore, abnormal Tau can recruit the properly folded isoform into misfolded complexes and, the abnormal form can be secreted from one cell and be taken up by other cells, which can trigger a cascade of misfolded Tau complexes.

Immunotherapy for the reduction in the intracellular levels of tau available for misfolding and/or aggregation represents a potential therapeutic approach for the treatment of tauopathies. Full-length antibodies that bind tau, however, have limited penetration into brain cells where tau protein aggregates reside.

SUMMARY

This disclosure features bi-functional polypeptides that specifically bind to tau and their use to treat and prevent tauopathies, such as Alzheimer's disease. The bi-functional polypeptides disclosed herein comprise a first domain comprising an antigen binding domain of an antibody or antigen binding functional fragment thereof which binds to an epitope of Tau. The bi-functional polypeptides disclosed herein further comprise a second domain comprising a proteasomal targeting PEST degron to enhance the degradation of tau following association with the bi-functional polypeptide. In one aspect, the disclosure provides an isolated bi-functional bi-functional polypeptide that specifically binds to tau, wherein the polypeptide comprises a first domain comprising an antigen binding domain of an antibody or antigen binding functional fragment thereof which binds to an epitope of Tau, and a second domain comprising a proteasome-targeting PEST motif. In some aspects, the bi-functional polypeptide is a single chain polypeptide.

In certain embodiments, the antigen binding domain of an antibody or functional antigen binding fragment thereof is selected from the group consisting of a Fab, a Fab', a F(ab')2, a Fv, a diabody, a scFv, and a sc(Fv)2.

In certain embodiments, the first domain is an intrabody.

In certain embodiments, the first domain is a single chain fragment (scFv) which binds to an epitope of tau. For example, in some embodiments, first domain is a scFv which comprises a tau specific VL domain ($V_L$Tau) and a Tau specific $V_H$ domain ($V_H$Tau).

In one aspect, a bi-functional polypeptide comprises a first domain that comprises a single chain fragment (scFv) which binds to an epitope of tau and a second domain comprising a proteasome-targeting PEST motif. In some embodiments, the domains are arranged in the order of $V_L$Tau-$V_H$Tau-PEST motif. In some embodiments, the domains are arranged in the order of $V_H$Tau-$V_L$Tau-PEST motif.

The PEST motif may be derived from either mouse or human short-lived proteins, such as ornithine decarboxylase (ODC).

In certain embodiments, this disclosure features a bi-functional polypeptide comprising a first domain, wherein the first domain comprises an antigen binding domain of an antibody or functional fragment thereof.

In some embodiments, the bi-functional polypeptide comprises a first domain is a single chain fragment (scFv) which binds to an epitope of tau, the scFv comprising a Tau specific $V_L$ domain ($V_L$ Tau) and a Tau specific $V_H$ domain ($V_H$ Tau).

In some embodiments, the scFv comprises a Tau specific $V_L$ domain ($V_L$ Tau) or antigen binding fragment thereof having an amino acid sequence that is:
  BEGIN HERE at least 80%, at least 85%, at least 90%, at least 95%, at least 96%, at least 97%, at least 98%, at least 99% or 100% identical to an amino acid sequence as set forth in SEQ ID NO: 18;
  at least 80%, at least 85%, at least 90%, at least 95%, at least 96%, at least 97%, at least 98%, at least 99% or 100% identical to an amino acid sequence as set forth in SEQ ID NO: 19;

at least 80%, at least 85%, at least 90%, at least 95%, at least 96%, at least 97%, at least 98%, at least 99% or 100% identical to an amino acid sequence as set forth in SEQ ID NO: 20;

at least 80%, at least 85%, at least 90%, at least 95%, at least 96%, at least 97%, at least 98%, at least 99% or 100% identical to an amino acid sequence as set forth in SEQ ID NO: 21;

at least 80%, at least 85%, at least 90%, at least 95%, at least 96%, at least 97%, at least 98%, at least 99% or 100% identical to an amino acid sequence as set forth in SEQ ID NO: 22;

at least 80%, at least 85%, at least 90%, at least 95%, at least 96%, at least 97%, at least 98%, at least 99% or 100% identical an amino acid sequence as set forth in SEQ ID NO: 23;

at least 80%, at least 85%, at least 90%, at least 95%, at least 96%, at least 97%, at least 98%, at least 99% or 100% identical to an amino acid sequence as set forth in SEQ ID NO: 24;

at least 80%, at least 85%, at least 90%, at least 95%, at least 96%, at least 97%, at least 98%, at least 99% or 100% identical to an amino acid sequence as set forth in SEQ ID NO: 25;

at least 80%, at least 85%, at least 90%, at least 95%, at least 96%, at least 97%, at least 98%, at least 99% or 100% identical to an amino acid sequence as set forth in SEQ ID NO: 26;

at least 80%, at least 85%, at least 90%, at least 95%, at least 96%, at least 97%, at least 98%, at least 99% or 100% identical to an amino acid sequence as set forth in SEQ ID NO: 27;

at least 80%, at least 85%, at least 90%, at least 95%, at least 96%, at least 97%, at least 98%, at least 99% or 100% identical to an amino acid sequence as set forth in SEQ ID NO: 28;

at least 80%, at least 85%, at least 90%, at least 95%, at least 96%, at least 97%, at least 98%, at least 99% or 100% identical to an amino acid sequence as set forth in SEQ ID NO: 29;

at least 80%, at least 85%, at least 90%, at least 95%, at least 96%, at least 97%, at least 98%, at least 99% or 100% identical to an amino acid sequence as set forth in SEQ ID NO: 30;

at least 80%, at least 85%, at least 90%, at least 95%, at least 96%, at least 97%, at least 98%, at least 99% or 100% identical to an amino acid sequence as set forth in SEQ ID NO: 31;

at least 80%, at least 85%, at least 90%, at least 95%, at least 96%, at least 97%, at least 98%, at least 99% or 100% identical to an amino acid sequence as set forth in SEQ ID NO: 32;

at least 80%, at least 85%, at least 90%, at least 95%, at least 96%, at least 97%, at least 98%, at least 99% or 100% identical to an amino acid sequence as set forth in SEQ ID NO: 33; or at least 80%, at least 85%, at least 90%, at least 95%, at least 96%, at least 97%, at least 98%, at least 99% or 100% identical to an amino acid sequence as set forth in SEQ ID NO: 34.

In some embodiments, the scFv comprises a Tau specific $V_H$ domain ($V_H$ Tau) or antigen binding fragment thereof having an amino acid sequence that is:

at least 80%, at least 85%, at least 90%, at least 95%, at least 96%, at least 97%, at least 98%, at least 99% or 100% identical to an amino acid sequence as set forth in SEQ ID NO: 1;

at least 80%, at least 85%, at least 90%, at least 95%, at least 96%, at least 97%, at least 98%, at least 99% or 100% identical to an amino acid sequence as set forth in SEQ ID NO: 2;

at least 80%, at least 85%, at least 90%, at least 95%, at least 96%, at least 97%, at least 98%, at least 99% or 100% identical to an amino acid sequence as set forth in SEQ ID NO: 3;

at least 80%, at least 85%, at least 90%, at least 95%, at least 96%, at least 97%, at least 98%, at least 99% or 100% identical to an amino acid sequence as set forth in SEQ ID NO: 4;

at least 80%, at least 85%, at least 90%, at least 95%, at least 96%, at least 97%, at least 98%, at least 99% or 100% identical to an amino acid sequence as set forth in SEQ ID NO: 5;

at least 80%, at least 85%, at least 90%, at least 95%, at least 96%, at least 97%, at least 98%, at least 99% or 100% identical to an amino acid sequence as set forth in SEQ ID NO: 6;

at least 80%, at least 85%, at least 90%, at least 95%, at least 96%, at least 97%, at least 98%, at least 99% or 100% identical to an amino acid sequence as set forth in SEQ ID NO: 7;

at least 80%, at least 85%, at least 90%, at least 95%, at least 96%, at least 97%, at least 98%, at least 99% or 100% identical to an amino acid sequence as set forth in SEQ ID NO: 8;

at least 80%, at least 85%, at least 90%, at least 95%, at least 96%, at least 97%, at least 98%, at least 99% or 100% identical to an amino acid sequence as set forth in SEQ ID NO: 9;

at least 80%, at least 85%, at least 90%, at least 95%, at least 96%, at least 97%, at least 98%, at least 99% or 100% identical to an amino acid sequence as set forth in SEQ ID NO: 10;

at least 80%, at least 85%, at least 90%, at least 95%, at least 96%, at least 97%, at least 98%, at least 99% or 100% identical to an amino acid sequence as set forth in SEQ ID NO: 11;

at least 80%, at least 85%, at least 90%, at least 95%, at least 96%, at least 97%, at least 98%, at least 99% or 100% identical to an amino acid sequence as set forth in SEQ ID NO: 12;

at least 80%, at least 85%, at least 90%, at least 95%, at least 96%, at least 97%, at least 98%, at least 99% or 100% identical to an amino acid sequence as set forth in SEQ ID NO: 13;

at least 80%, at least 85%, at least 90%, at least 95%, at least 96%, at least 97%, at least 98%, at least 99% or 100% identical to an amino acid sequence as set forth in SEQ ID NO: 14;

at least 80%, at least 85%, at least 90%, at least 95%, at least 96%, at least 97%, at least 98%, at least 99% or 100% identical to an amino acid sequence as set forth in SEQ ID NO: 15;

at least 80%, at least 85%, at least 90%, at least 95%, at least 96%, at least 97%, at least 98%, at least 99% or 100% identical to an amino acid sequence as set forth in SEQ ID NO: 16; or at least 80%, at least 85%, at least 90%, at least 95%, at least 96%, at least 97%, at least 98%, at least 99% or 100% identical to an amino acid sequence as set forth in SEQ ID NO: 17.

In certain embodiments, the Tau specific VL domain ($V_L$ Tau) and a Tau specific $V_H$ domain ($V_H$ Tau) are connected via a linker. For example, the Tau specific VL domain ($V_L$ Tau) and a Tau specific VH domain ($V_H$ Tau) are connected via a linker that has an amino acid sequence that is at least 80%, at least 85%, at least 90%, at least 95%, at least 96%, at least 97%, at least 98%, at least 99% or 100% identical to an amino acid set forth in SEQ ID NO: 35 (GGGGSGGGGSGGGGS) or SEQ ID NO: 37 (YPYDVPDYA).

In certain embodiments, this disclosure features a bi-functional polypeptide comprising a second domain, wherein the second domain comprises a proteasome-targeting PEST motif that has an amino acid sequence that is at least 80%, at least 85%, at least 90%, at least 95%, at least 96%, at least 97%, at least 98%, at least 99% or 100% identical to an amino acid set forth in SEQ ID NO: 36 (SHGFPPEVEEQDDGTLPMSCAQESGMDRH-PAACASARIN).

In certain embodiments, this disclosure features a bi-functional polypeptide comprising a second domain, wherein the second domain comprises a proteasome-targeting PEST motif corresponding to the human $ODC_{422-461}$ PEST having an amino acid sequence that is at least 80%, at least 85%, at least 90%, at least 95%, at least 96%, at least 97%, at least 98%, at least 99% or 100% identical to an amino acid set forth in SEQ ID NO: 38 (NPDFPPEVEEQ-DASTLPVSCAWESGMKRHRAACASASINV).

In certain embodiments, this disclosure features a bi-functional polypeptide comprising a second domain, wherein the second domain comprises a proteasome-targeting PEST motif corresponding to the human $ODC_{422-461}$ PEST having an amino acid sequence that is at least 80%, at least 85%, at least 90%, at least 95%, at least 96%, at least 97%, at least 98%, at least 99% or 100% identical to an amino acid set forth in SEQ ID NO: 39 (SHGFPPEVE-EQDDGTLPMSCAQESGMDRHPAACASARINV).

In certain embodiments, the first and second domain are connected by a polypeptide linker. One such polypeptide linker comprises an amino acid sequence having at least 80% identity to SEQ ID NO: 3.

In certain embodiments, the first domain is a single-chain fragment (scFv) of an anti-tau antibody.

In certain embodiments, the first domain is a single domain antibody (dAb; either $V_H$ or $V_L$) of the antibody which binds to an epitope of Tau.

In some embodiments, the first domain binds to an epitope comprising amino acids 312-322 of SEQ ID NO: 7. In some embodiment, the first domain binds to an epitope comprising amino acids 150 to 190 of SEQ ID NO: 7.

In another aspect, the disclosure provides a polynucleotide encoding single-chain bi-functional polypeptide which comprises a first domain comprising an antigen binding domain of an antibody or functional fragment thereof which binds to an epitope of Tau; and a second domain comprising a proteasome-targeting PEST motif The polynucleotides can be incorporated into a vector. Also contemplated are isolated host cells transfected with a polynucleotide or vector described herein.

In another aspect, the disclosure provides an isolated nucleic acid comprising a nucleotide sequence that encodes an amino acid sequence that is at least 80%, at least 85%, at least 90%, at least 95%, at least 96%, at least 97%, at least 98%, at least 99% or 100% identical to an amino acid sequence set forth in SEQ ID Nos: 1-34. The proteins encoded by these nucleic acids specifically bind to tau. This disclosure also includes proteins encoded by any of the above nucleic acids. In addition, this disclosure includes recombinant vectors comprising any of the above nucleic acids. Furthermore, this application provides host cells comprising recombinant vectors comprising any of the above nucleic acids.

In yet another aspect, this disclosure features a method of preparing a bi-functional polypeptide of the present disclosure, which method comprises culturing a host cell comprising recombinant vectors comprising the nucleic acid sequence encoding single-chain bi-functional polypeptide which comprises a first domain comprising an antigen binding domain of an antibody or functional fragment thereof which binds to an epitope of Tau; and a second domain comprising a proteasome-targeting PEST motif under conditions appropriate for expression of a polypeptide, wherein the polypeptide and a bi-functional polypeptide are both expressed. In certain embodiments, the method further involves isolating the bi-functional polypeptide. In some embodiments, the host cell is a CHO, 293E, or COS cell.

In certain embodiments, the antibody is monoclonal antibody, a synthetic antibody, a human or a humanized antibody.

In some embodiments, the bi-functional polypeptide is used to treat or prevent a tauopathy in a patient in need thereof, the use comprising administering to the patient the bi-functional polypeptide.

In one aspect, the disclosure provides methods of treating and preventing a tauopathy of a patient in need thereof.

In another aspect, the disclosure provides methods for the preparation of a single-chain bi-functional polypeptide, which methods comprise cultivating a host cell transfected with a polynucleotide which upon expression encodes a single-chain bi-functional polypeptide as described herein; and isolating the polypeptide from the cell.

In yet a further aspect, the disclosure provides compositions comprising a single-chain bi-functional polypeptide, the bi-functional polypeptide comprising a first domain comprising an antigen binding domain of an antibody or functional fragment thereof which binds to an epitope of Tau; and a second domain comprising a proteasome-targeting PEST motif. In some embodiments, the composition is a pharmaceutical composition further comprising a pharmaceutically acceptable carrier.

In certain embodiments, this disclosure features a bi-functional polypeptide that binds to an epitope of Tau, the bi-functional polypeptide comprising an amino acid sequence that is at least 80%, at least 85%, at least 90%, at least 95%, at least 97%, or 100% identical to any one of SEQ ID NOs: 40 to 56.

In certain embodiments, this disclosure features a bi-functional polypeptide that binds to an epitope of Tau, the bi-functional polypeptide comprising an amino acid sequence that is at least 80%, at least 85%, at least 90%, at least 95%, at least 97%, or 100% identical to any one of SEQ ID NOs: 57 to 73.

In another aspect, the disclosure provides an isolated nucleic acid comprising a nucleotide sequence that encodes an amino acid sequence that is at least 80%, at least 85%, at least 90%, at least 95%, at least 96%, at least 97%, at least 98%, at least 99% or 100% identical to an amino acid sequence set forth in SEQ ID NOs: 40 to 73.

In another aspect, the disclosure provides methods for the treatment of a tauopathy in a patient in need of such treatment, which comprises administering to the patient in need of such treatment an effective amount for treating the tauopathy of a single-chain bi-functional polypeptide, which comprises a first domain comprising an antigen binding domain of an antibody or fragment thereof which binds to an epitope of Tau; and a second domain comprising a proteasome-targeting PEST motif. Tauopathies that may be treated according to the method include, but are not limited to, Alzheimer disease (AD), Down syndrome, Guam parkinsonism dementia complex, Dementia pugilistica, Pick disease, Dementia with argyrophilic grains, Fronto-temporal dementia, Cortico-basal degeneration, Pallido-ponto-nigral degeneration, Progressive supranuclear palsy, and Gerstmann-Sträussler-Scheinker disease. The administering step can include administering to the patient a polynucleotide which upon expression encodes a single-chain bi-functional polypeptide which comprises a first domain comprising an antigen binding domain of an antibody or fragment thereof which binds to an epitope of Tau; and a second domain comprising a proteasome-targeting PEST motif. In some embodiments, treatment inhibits or slows down formation of tau aggregates in (the brain of, a cell of) the patient. In some embodiments, treatment inhibits or slows down formation of neurofibrillary tangles in (the brain of) the patient.

The present disclosure provides antigen-binding domains of an antibody or functional fragments thereof and similar antigen-binding molecules which are capable of specifically recognizing tau. By "specifically recognizing tau", "antibody specific to/for tau" and "anti-tau antibody" is meant specifically, generally, and collectively, antibodies to the native form of tau, phosphorylated forms of tau, or aggregated or pathologically modified tau isoforms Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

Figure 2:
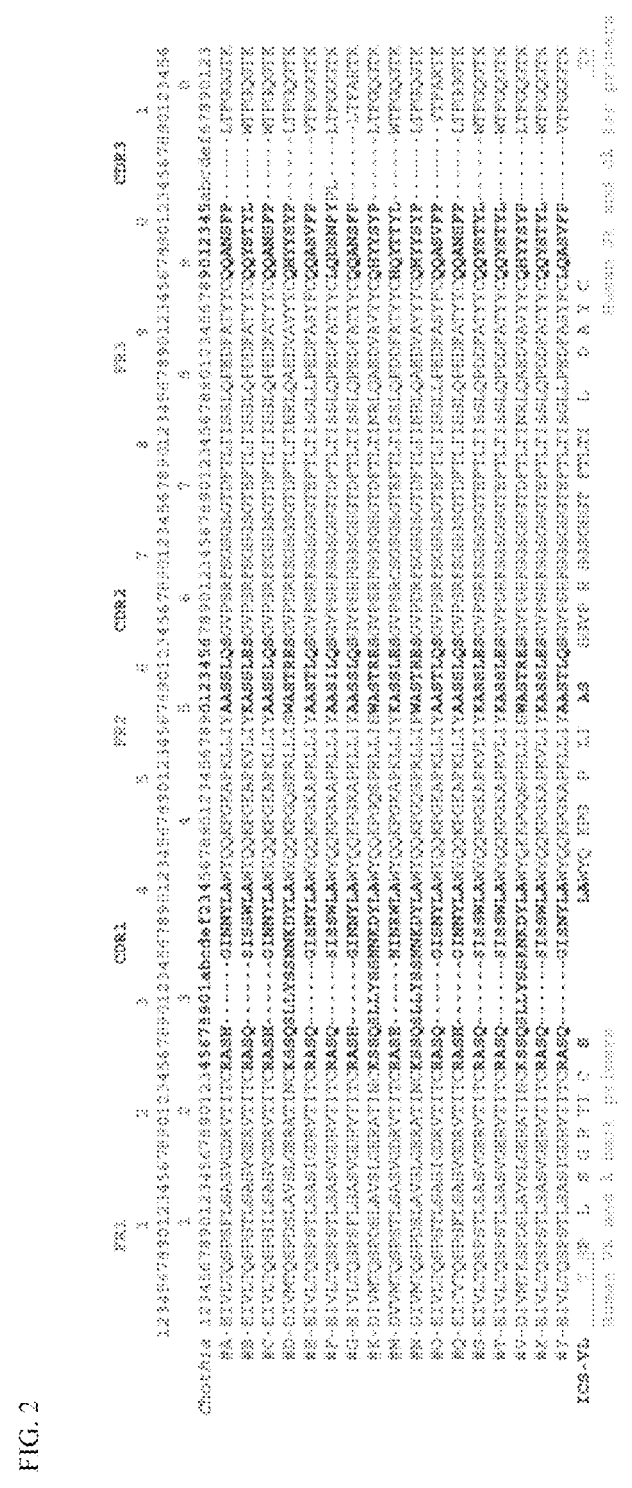

FIG. 2 is an alignment of seventeen anti-Tau light chain variable region amino acid sequences. The CDRs (according to Kabat) are in bold.

DETAILED DESCRIPTION

Figure 1:
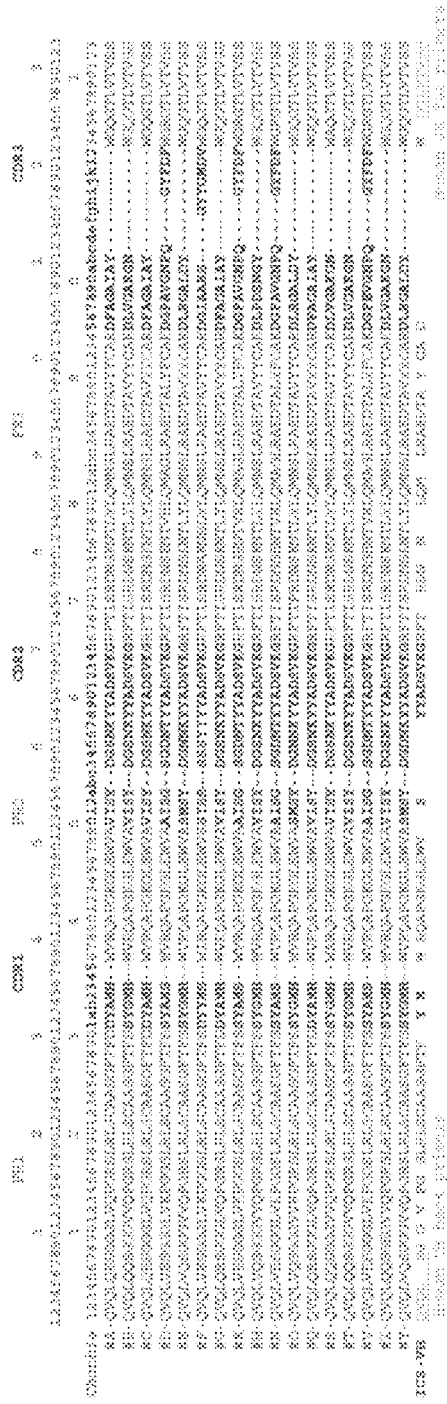
FIG. 1 is an alignment of seventeen anti-Tau heavy chain variable region amino acid sequences. The CDRs (according to Kabat) are in bold

This disclosure features polypeptides, e.g., bi-functional polypeptides, comprising an antigen binding domain of an antibody or functional fragment thereof, which binds to an epitope of Tau, and a proteasome-targeting PEST motif. The bi-functional polypeptides are useful in the treatment and prevention of tauopathies.

The antigen binding domain of an antibody or functional fragment thereof can bind to phosphorylated tau, hyperphosphorylated tau and/or aggregated tau with high specificity and/or high affinity. The amino acid sequence of the human tau protein (Genbank® Accession No. NP_001116538) is shown below:

(SEQ ID NO: 7)
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQEPESGKVVQEGFLREPGPPGLSHQLM

SGMPGAPLLPEGPREATRQPSGTGPEDTEGGRHAPELLKHQLLGDLHQEG

PPLKGAGGKERPGSKEEVDEDRDVDESSPQDSPPSKASPAQDGRPPQTAA

REATSIPGFPAEGAIPLPVDFLSKVSTEIPASEPDGPSVGRAKGQDAPLE

FTFHVEITPNVQKEQAHSEEHLGRAAFPGAPGEGPEARGPSLGEDTKEAD

LPEPSEKQPAAAPRGKPVSRVPQLKARMVSKSKDGTGSDDKKAKTSTRSS

AKTLKNRPCLSPKHPTPGSSDPLIQPSSPAVCPEPPSSPKYVSSVTSRTG

SSGAKEMKLKGADGKTKIATPRGAAPPGQKGQANATRIPAKTPPAPKTPP

SSATKQVQRRPPPAGPRSERGEPPKSGDRSGYSSPGSPGTPGSRSRTPSL

PTPPTREPKKVAVVRTPPKSPSSAKSRLQTAPVPMPDLKNVKSKIGSTEN

LKHQPGGGKVQIINKKLDLSNVQSKCGSKDNIKHVPGGGSVQIVYKPVDL

SKVTSKCGSLGNIHHKPGGGQVEVKSEKLDFKDRVQSKIGSLDNITHVPG

GGNKKIETHKLTFRENAKAKTDHGAEIVYKSPVVSGDTSPRHLSNVSSTG

SIDMVDSPQLATLADEVSASLAKQGL

As used herein, the term "antibody" includes intact immunoglobulins derived from natural sources or from recombinant sources, as well as immunoreactive portions (i.e., 'antigen binding domains' or 'antigen binding portions') of intact immunoglobulins. The antibodies of the present invention may exist in a variety of forms including, for example, polyclonal antibodies, monoclonal antibodies, intracellular antibodies ("intrabodies"), antibody fragments (e.g., Fv, Fab, Fab', and F(ab')2), as well as single chain antibodies (scFv), single domain $V_H$ or $V_L$ antibodies, chimeric antibodies, human antibodies and humanized antibodies.

Antibody fragments (e.g., Fv, Fab, Fab', and F(ab')2), such as antibody fragments of an anti-tau-binding antibody, may be prepared by proteolytic digestion of intact an antibody (e.g., and anti-tau antibody). For example, antibody fragments can be obtained by treating a whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

Alternatively, antibody fragments, such as antibody fragments of an anti-tau-binding antibody, can be produced recombinantly. For example, nucleic acids encoding the antibody fragments of interest can be constructed, introduced into an expression vector, and expressed in suitable host cells. See, e.g., Co, M. S. et al., *J. Immunol.*, 152:2968-

2976 (1994); Better, M. and Horwitz, A. H., *Methods in Enzymology*, 178:476-496 (1989); Pluckthun, A. and Skerra, A., *Methods in Enzymology*, 178:476-496 (1989); Lamoyi, E., *Methods in Enzymology*, 121:652-663 (1989); Rousseaux, J. et al., *Methods in Enzymology*, (1989) 121:663-669 (1989); and Bird, R. E. et al., *TIBTECH*, 9:132-137 (1991)). For example, antibody fragments can be expressed in and secreted from *E. coli*, thus allowing the facile production of large amounts of these fragments. According to another approach, antibody fragments can be isolated directly from recombinant host cell culture.

As used herein, the term "epitope" designates a specific amino acid sequence, modified amino acid sequence, or protein secondary or tertiary structure which is specifically recognized by an antibody. The terms "specifically recognizing," "specifically recognizes," and any grammatical variants mean that the antibody or antigen-binding molecule thereof is capable of specifically interacting with and/or binding to at least two, at least three, or at least four amino acids of an epitope, e.g., a Tau epitope. Such binding can be exemplified by the specificity of a "lock-and-key-principle." Thus, specific motifs in the amino acid sequence of the antigen-binding domain the tau antibody or antigen-binding molecule thereof and the epitope bind to each other as a result of their primary, secondary or tertiary structure as well as the result of secondary modifications of the structure.

As used herein "intrabody" means an intracellular or antibody fragment that can induce a phenotypic knockout, work as a neutralizing agent by direct binding to the target antigen, alter protein folding, protein-protein, protein-DNA, protein-RNA interactions and protein modification intracellularly.

The antigen binding domain of an antibody or functional fragment thereof of the present disclosure include single chain (scFv), single-chain (Fv)2 (sc(Fv)2), single domain antibodies (dAb; $V_H$; $V_L$), and diabodies. scFV and single domain antibodies retain the binding specificity of full-length antibodies, but they can be expressed as single genes. scFV and single domain $V_H$ or $V_L$ antibodies may be applied both extracellularly and intracellularly (intrabodies).

An scFv is a single-chain polypeptide antibody obtained by linking the $V_H$ and $V_L$ of an antibody with a linker (see e.g., Huston et al., *Proc. Natl. Acad. Sci. U S. A.*, 85:5879-5883 (1988); and Pluckthun, "The Pharmacology of Monoclonal Antibodies" Vol. 113, Ed Resenburg and Moore, Springer Verlag, New York, pp. 269-315, (1994)). The order of $V_H$S and $V_L$S to be linked is not particularly limited, and they may be arranged in any order. Examples of arrangements include: [$V_H$]-linker-[$V_L$]; or [$V_L$]-linker-[$V_H$]. The heavy chain variable region ($V_H$) and light chain variable region ($V_L$) in an scFv may be derived from any anti-tau antibody or antigen-binding fragment thereof described herein.

An sc(Fv)2 contains two $V_H$s and two $V_L$s which are linked by a linker to form a single chain (Hudson, et al., *J. Immunol. Methods*, (1999) 231: 177-189 (1999)). An sc(Fv)2 can be prepared, for example, by connecting scFvs with a linker. sc(Fv)2s may include two $V_H$s and two $V_L$s arranged in the order of: $V_H$, $V_L$, $V_H$, and $V_L$ ([$V_H$]-linker-[$V_L$]-linker-[$V_H$]-linker-[$V_L$]), beginning from the N terminus of a single-chain polypeptide; however, the order of the two $V_H$s and two $V_L$s is not limited to the above arrangement, and they may be arranged in any order. Examples of arrangements are listed below:

[$V_L$]-linker-[$V_H$]-linker-[$V_H$]-linker-[$V_L$]
[$V_H$]-linker-[$V_L$]-linker-[$V_L$]-linker-[$V_H$]
[$V_H$]-linker-[$V_H$]-linker [$V_L$]-linker-[$V_L$]
[$V_L$]-linker-[$V_L$]-linker-[$V_H$]-linker-[$V_H$]
[$V_L$]-linker-[$V_H$]-linker-[$V_L$]-linker-[$V_H$]

Normally, three linkers are required when four antibody variable regions are linked; the linkers used may be identical or different. There is no particular limitation on the linkers that link the $V_H$ and $V_L$ regions of the scFVs or sc(FV)2s. In some embodiments, the linker is a peptide linker. Any arbitrary single-chain peptide comprising about three to 25 residues (e.g., 5, 6, 7, 8, 9, 10, 11, 12, 13, 14, 15, 16, 17, 18) can be used as a linker.

The amino acid sequence of the $V_H$ or $V_L$ in the antigen binding domain of an antibody or functional fragment thereof may include modifications such as substitutions, deletions, additions, and/or insertions. For example, modifications, such as substitutions, deletions, additions, and/or insertions, made within the amino acid sequence of the $V_H$ or $V_L$ may be in one or more of the CDRs. In certain embodiments, the modification involves one, two, or three amino acid substitutions in one or more CDRs and/or framework regions of the $V_H$ and/or $V_L$ domain of the anti-tau antigen binding domain of an antibody or functional fragment thereof. Such substitutions are made to improve the binding, functional activity and/or reduce immunogenicity of the anti-tau antigen binding domain of an antibody or functional fragment thereof. In certain embodiments, the substitutions are conservative amino acid substitutions. In some embodiments, one, two, or three amino acids of the CDRs of the anti-tau antigen binding domain of an antibody or functional fragment thereof may be deleted or added, so as long as there is tau binding and/or functional activity when $V_H$ and $V_L$ are associated.

The proteasome-targeting PEST motif is a peptide sequence containing regions enriched in prolyl (P), glutamyl (E), aspartyl (D), seryl (S) and threonyl (T) residues (PEST regions) and are targeted for accelerated proteasomal degradation. This sequence is associated with proteins that have a short intracellular half-life. Mouse Ornithine DeCarboxylase (MODC) is one of the shortest half-lived proteins in mammals. The constitutive degradation of MODC by the proteasome is controlled by PEST sequences in its carboxy terminus (amino acids 422-461).

Exemplary murine derived PEST motif sequences include, for example, an amino acid sequence at least 80%, at least 85%, at least 90%, at least 95%, at least 96%, at least 97%, at least 98%, at least 99% or 100% identical to an amino acid sequence as set forth in SEQ ID NO: 36 (SHGFPPEVEEQDDGTLPMSCAQESGMDRH-PAACASARIN) and SEQ ID NO: 39 (SHGFPPEVE-EQDDGTLPMSCAQESGMDRHPAACASARINV).

Exemplary human derived PEST motif sequences (hPEST) include, for example, an amino acid sequence at least 80%, at least 85%, at least 90%, at least 95%, at least 96%, at least 97%, at least 98%, at least 99% or 100% identical to an amino acid sequence as set forth in SEQ ID NO: 38 (NPDFPPEVEEQDASTLPVS-CAWESGMKRHRAACASASINV).

A comparison of mouse PEST (mPEST; SEQ ID NO: 39) and human PEST (hPEST; SEQ ID NO: 38) sequences is provided in Table 1, demonstrating 82.5% sequence homology between mouse mPEST and human hPEST.

TABLE 1

| | Sequence |
|---|---|
| mPEST (ODC-$_{PEST422-461}$) | SHGFPPEVEEQDDGTLPMSCAQESGMDRHPAA CASARINV (SEQ ID NO: 39) |
| hPEST (ODC-PEST422-461) | NPDFPPEVEEQDASTLPVSCAWESGMKRHRAA CASASINV (SEQ ID NO: 38) |

The term "% identical" between two polypeptide (or polynucleotide) sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence. One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org (ClustalX is a version of the ClustalW2 program ported to the Windows environment). Another suitable program is MUSCLE, available from www.drive5.com/muscle. ClustalW2 and MUSCLE are alternatively available, e.g., from the EBI.

The terms "linked" or "fused" refers to linkage via a peptide bonds (e.g., genetic fusion), chemical conjugation, or other means known in the art. For example, one way in which molecules or moieties can be linked employs peptide linkers that link the molecules or moieties via peptide bonds.

The term "associated with" refers to a covalent or non-covalent bond formed between a first amino acid chain and a second amino acid chain. In one embodiment, the term "associated with" means a covalent, non-peptide bond or a non-covalent bond. In another embodiment, the term "associated with" refers to a covalent, non-peptide bond or a non-covalent bond that is not chemically crosslinked. In another embodiment, it means a covalent bond except a peptide bond. In some embodiments this association is indicated by a colon, i.e., (:).

Method of Producing Polypeptides

The bi-functional polypeptides (or antigen binding domain of an antibody or functional fragment thereof) of this disclosure may be produced in bacterial or eukaryotic cells. To produce the polypeptide of interest, a polynucleotide encoding the polypeptide is constructed, introduced into an expression vector, and then expressed in suitable host cells. Standard molecular biology techniques are used to prepare the recombinant expression vector, transfect the host cells, select for transformants, culture the host cells and recover the antibody.

If the polypeptide is to be expressed in bacterial cells (e.g., *E. coli*), the expression vector should have characteristics that permit amplification of the vector in the bacterial cells. Additionally, when *E. coli* such as JM109, DHSα, HB101, or XL1-Blue is used as a host, the vector must have a promoter, for example, a lacZ promoter (Ward et al., 341:544-546 (1989), araB promoter (Better et al., *Science*, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., *J. Bacteriol.*, 169:4379 (1987)) may be used as the signal sequence for antibody secretion. For bacterial expression, calcium chloride methods or electroporation methods may be used to introduce the expression vector into the bacterial cell.

In one embodiment, the polypeptides are produced in mammalian cells. Exemplary mammalian host cells for expressing a polypeptide include Chinese Hamster Ovary (CHO cells) (including dhfr⁻ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal.

If the polypeptide is to be expressed in mammalian cells such as CHO, COS, 293, 293T, and NIH3T3 cells, the expression vector includes a promoter necessary for expression in these cells, for example, an SV40 promoter (Mulligan et al., Nature, 277:108 (1979)), MMLV-LTR promoter, EF1α promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

The polypeptides of the present disclosure can be isolated from inside or outside (such as medium) of the host cell and purified as substantially pure and homogenous antibodies. Methods for isolation and purification commonly used for polypeptides purification may be used for the isolation and purification of polypeptides, and are not limited to any particular method. Polypeptides may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes polypeptides that are highly purified using these purification methods.

Characterization of the Antigen Binding Domain of an Antibody or Antigen Binding Functional Fragment Thereof The tau-binding properties of the polypeptides described herein may be measured by any standard method, e.g., one or more of the following methods: OCTET®, Surface Plasmon Resonance (SPR), BIACORE™ analysis, Enzyme Linked Immunosorbent Assay (ELISA), EIA (enzyme immunoassay), RIA (radioimmunoassay), and Fluorescence Resonance Energy Transfer (FRET).

The binding interaction of a protein of interest (an anti-tau antibody binding domain or functional fragment thereof) and a target (e.g., Tau) can be analyzed using the OCTET® systems. In this method, one of several variations of instruments (e.g., OCTET® QKe and QK), made by the FortéBio company are used to determine protein interactions, binding specificity, and epitope mapping. The OCTET® systems provide an easy way to monitor real-time binding by measuring the changes in polarized light that travels down a custom tip and then back to a sensor.

The binding interaction of a protein of interest (an anti-tau antibody binding domain or functional fragment thereof) and a target (e.g., tau) can be analyzed using Surface Plasmon Resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which is measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Information from SPR can be used to provide an accurate and quantitative measure of the equilibrium dissociation constant ($K_d$), and kinetic parameters, including $K_{on}$ and $K_{off}$, for the binding of a biomolecule to a target.

Epitopes can also be directly mapped by assessing the ability of different anti-tau antibody binding domains or functional fragment thereof to compete with each other for binding to human tau using BIACORE chromatographic techniques (Pharmacia BIAtechnology Handbook, "Epitope Mapping", Section 6.3.2, (May 1994); see also Johne et al. (1993) *J. Immunol. Methods,* 160:191-198).

When employing an enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Additional general guidance for evaluating antibodies, e.g., Western blots and immunoprecipitation assays, can be found in *Antibodies: A Laboratory Manual*, ed. by Harlow and Lane, Cold Spring Harbor press (1988)).

Methods of Treatment

The bi-functional polypeptides described herein can be used in the treatment, including prevention, of tauopathies, such as, but not limited to Alzheimer's disease (AD), Fronto-temporal Dementia with Parkinsonism on chromosome-17 (FTDP-17), Pick's disease, Corticobasal Degeneration (CBD), Progressive Supranuclear Palsy (PSP), Dementia pugilistica (chronic traumatic encephalopathy), Lytico-Bodig disease, Ganglioglioma and gangliocytoma, Meningioangiomatosis, Subacute sclerosing panencephalitis, Llead encephalopathy, Tuberous sclerosis and Hallervorden-Spatz disease. Such methods comprise administering to a subject in need thereof (e.g., a subject suffering from or at risk of having a tauopathy) a therapeutically effective amount of a bi-functional polypeptide, which comprises a first domain comprising an antigen binding domain of an antibody or fragment thereof which binds to an epitope of tau; and a second domain comprising a proteasome-targeting PEST motif.

The term "subject" refers to an animal or human, or to one or more cells derived from an animal or human. Preferably, the subject is a human. Subjects can also include non-human primates.

Pharmaceutical Compositions

A bi-functional polypeptide as described herein can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) *J. Pharm. Sci.* 66:1-19).

Pharmaceutical Formulation is a Well-Established.

Pharmaceutical formulation is a well-established art, and is further described, e.g., in Gennaro (ed.), *Remington: The Science and Practice of Pharmacy,* 20$^{th}$ ed., Lippincott, Williams & Wilkins (2000) (ISBN: 0683306472); Ansel et al., *Pharmaceutical Dosage Forms and Drug Delivery Systems,* 7$^{th}$ Ed., Lippincott Williams & Wilkins Publishers (1999) (ISBN: 0683305727); and Kibbe (ed.), *Handbook of Pharmaceutical Excipients American Pharmaceutical Association,* 3$^{rd}$ ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, a bi-functional polypeptide described herein is formulated with excipient materials, such as sodium citrate, sodium dibasic phosphate heptahydrate, sodium monobasic phosphate, Tween-80, and a stabilizer. It can be provided, for example, in a buffered solution at a suitable concentration and can be stored at 2-8° C. In some other embodiments, the pH of the composition is between about 5.5 and 7.5 (e.g., 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5).

The pharmaceutical compositions can also include agents that reduce aggregation of the bi-functional polypeptide when formulated. Examples of aggregation reducing agents include one or more amino acids selected from the group consisting of methionine, arginine, lysine, aspartic acid, glycine, and glutamic acid. These amino acids may be added to the formulation to a concentration of about 0.5 mM to about 145 mM (e.g., 0.5 mM, 1 mM, 2 mM, 5 mM, 10 mM, 25 mM, 50 mM, 100 mM). The pharmaceutical compositions can also include a sugar (e.g., sucrose, trehalose, mannitol, sorbitol, or xylitol) and/or a tonicity modifier (e.g., sodium chloride, mannitol, or sorbitol) and/or a surfactant (e.g., polysorbate-20 or polysorbate-80).

Such compositions can be administered by a parenteral mode (e.g., intravenous, subcutaneous, intraperitoneal, or intramuscular injection). In one embodiment, the bi-functional polypeptide compositions are administered subcutaneously. In one embodiment, the bi-functional polypeptide compositions are administered intravenously. The phrases "parenteral administration" and "administered parenterally" as used herein mean modes of administration other than enteral and topical administration, usually by injection, and include, without limitation, intravenous, intramuscular, intraarterial, intrathecal, intracapsular, intraocular, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the bi-functional polypeptide may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems,* J. R. Robinson, ed., Marcel Dekker, Inc., New York (1978).

In one embodiment, the pharmaceutical formulation comprises a bi-functional polypeptide at a concentration of about 0.5 mg/mL to 500 mg/mL (e.g., 0.5 mg/mL, 1 mg/mL, 5 mg/mL, 10 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 250 mg/mL, 300 mg/mL, 350 mg/mL, 400 mg/mL, 450 mg/mL, 500 mg/mL), formulated with a pharmaceutically acceptable carrier. In some embodiments, the bi-functional polypeptide is formulated in sterile distilled water or phosphate buffered saline. The pH of the pharmaceutical formulation may be between 5.5 and 7.5 (e.g., 5.5, 5.6, 5.7, 5.8, 5.9, 6.0, 6.1, 6.2 6.3, 6.4 6.5, 6.6 6.7, 6.8, 6.9 7.0, 7.1, 7.3, 7.4, 7.5).

Administration

The bi-functional polypeptide can be administered to a subject, e.g., a subject in need thereof, for example, a human or animal subject, by a variety of methods. For many applications, the route of administration is one of: intravenous injection or infusion (IV), subcutaneous injection (SC), intraperitoneally (IP), or intramuscular injection. Other modes of parenteral administration can also be used. Examples of such modes include: intraarterial, intrathecal, intracapsular, intraocular, intracardiac, intradermal, transtracheal, subcuticular, intraarticular, subcapsular, subarachnoid, intraspinal, and epidural and intrasternal injection.

The route and/or mode of administration of the bi-functional polypeptide can also be tailored for the individual case, e.g., by monitoring the subject.

The bi-functional polypeptide can be administered as a fixed dose, or in a mg/kg dose. The dose can also be chosen to reduce or avoid production of antibodies against the bi-functional polypeptide. Dosage regimens are adjusted to provide the desired response, e.g., a therapeutic response or a combinatorial therapeutic effect. Generally, doses of the bi-functional polypeptide (and optionally a second agent) can be used in order to provide a subject with the agent in bioavailable quantities. For example, doses in the range of 0.1-100 mg/kg, 0.5-100 mg/kg, 1-100 mg/kg, 0.5-20 mg/kg, 0.1-10 mg/kg, or 1-10 mg/kg can be administered. Other doses can also be used. In certain embodiments, a subject in need of treatment with a bi-functional polypeptide is administered the bi-functional polypeptide at a dose of between about 1 mg/kg to about 30 mg/kg. In some embodiments, a subject in need of treatment with bi-functional polypeptide is administered the bi-functional polypeptide at a dose of 1 mg/kg, 2 mg/kg, 4 mg/kg, 5 mg/kg, 7 mg/kg 10 mg/kg, 12 mg/kg, 15 mg/kg, 20 mg/kg, 25 mg/kg, 28 mg/kg, 30 mg/kg, 35 mg/kg, 40 mg/kg, or 50 mg/kg. In a specific embodiment, the bi-functional polypeptide is administered subcutaneously at a dose of 1 mg/kg to 3 mg/kg. In another embodiment, the bi-functional polypeptide is administered intravenously at a dose of between 4 mg/kg and 30 mg/kg.

A composition may comprise about 1 mg/mL to 100 mg/ml or about 10 mg/mL to 100 mg/ml or about 50 to 250 mg/mL or about 100 to 150 mg/ml or about 100 to 250 mg/ml of the bi-functional polypeptide.

Dosage unit form or "fixed dose" as used herein refers to physically discrete units suited as unitary dosages for the subjects to be treated; each unit contains a predetermined quantity of bi-functional polypeptide calculated to produce the desired therapeutic effect in association with the required pharmaceutical carrier and optionally in association with the other agent. Single or multiple dosages may be given. Alternatively, or in addition, the bi-functional polypeptide may be administered via continuous infusion.

A bi-functional polypeptide dose can be administered, e.g., at a periodic interval over a period of time (a course of treatment) sufficient to encompass at least 2 doses, 3 doses, 5 doses, 10 doses, or more, e.g., once or twice daily, or about one to four times per week, or preferably weekly, biweekly (every two weeks), every three weeks, monthly, e.g., for between about 1 to 12 weeks, preferably between 2 to 8 weeks, more preferably between about 3 to 7 weeks, and even more preferably for about 4, 5, or 6 weeks. Factors that may influence the dosage and timing required to effectively treat a subject, include, e.g., the stage or severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments.

If a subject is at risk for developing a disorder described herein, the bi-functional polypeptide can be administered before the full onset of the disorder, e.g., as a preventative measure. The duration of such preventative treatment can be a single dosage of the bi-functional polypeptide or the treatment may continue (e.g., multiple dosages). For example, a subject at risk for the disorder or who has a predisposition for the disorder may be treated with the bi-functional polypeptide for days, weeks, months, or even years so as to prevent the disorder from occurring or fulminating.

A pharmaceutical composition may include a "therapeutically effective amount" of a bi-functional polypeptide as described herein. The term "therapeutically effective amount", "pharmacologically effective dose", "pharmacologically effective amount," or simply "effective amount" may be used interchangeably and refers to that amount of an agent effective to produce the intended pharmacological, therapeutic or preventive result. The pharmacologically effective amount results in the amelioration of one or more symptoms of a disorder, or prevents the advancement of a disorder, or causes the regression of the disorder, or prevents the disorder. Such effective amounts can be determined based on the effect of the administered agent, or the combinatorial effect of agents if more than one agent is used. A therapeutically effective amount of an agent may also vary according to factors such as the disease stage, state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

In certain embodiments, the bi-functional polypeptide is administered subcutaneously at a concentration of about 1 mg/mL to about 500 mg/mL (e.g., 1 mg/mL, 2 mg/mL, 3 mg/mL 4 mg/mL 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 400 mg/mL, 450 mg/mL). In one embodiment, the bi-functional polypeptide is administered subcutaneously at a concentration of 50 mg/mL. In another embodiment, the bi-functional polypeptide is administered intravenously at a concentration of about 1 mg/mL to about 500 mg/mL. In a particular embodiment, the bi-functional polypeptide is administered intravenously at a concentration of 50 mg/mL.

The bi-functional polypeptide can be administered to a patient in need thereof (e.g., a patient that has had or is at risk of having a tauopathy) alone or in combination with (i.e., by co-administration or sequential administration) other therapeutic proteins (e.g., antibodies, intrabodies, polypeptides) useful for treating a tauopathies may be desirable. In one embodiment, the additional therapeutic proteins are included in the pharmaceutical composition of the present invention. Examples of therapeutic proteins which can be used to treat a subject include, but are not limited to, therapeutic proteins targeting beta-amyloid, alpha-synuclein, TDP-43 and SOD-1.

The bi-functional polypeptide can be administered to a patient in need thereof (e.g., a patient that has or is at risk of having a tauopathy) in combination with (i.e., by co-administration or sequential administration) other neuroprotective agents useful for treating a tauopathy. In one embodiment, the additional agent is comprised of the pharmaceutical composition of the present invention. Examples of neuroprotective agents include, but are not limited to, an acetylcholinesterase inhibitor, a glutamatergic receptor antagonist, kinase inhibitors, HDAC inhibitors, anti-inflammatory agents, divalproex sodium, dopamine or a dopamine receptor agonist, or any combination thereof.

In some aspects, the bi-functional polypeptide described herein can be used in methods designed to express the bi-functional polypeptide intracellularly so as to bind intracellular tau. Such methods comprise delivering to a cell a bi-functional polypeptide which may be in any form used by one skilled in the art, for example, a protein, an RNA molecule which is translated, or a DNA vector which is transcribed and translated.

In instances where a polynucleotide molecule encoding a bi-functional polypeptide is used, the polynucleotide may be recombinantly engineered into a variety of host vector systems that can be introduced in vivo such that it is taken up by a cell and directs the transcription of the bi-functional polypeptide molecule. Such a vector can remain episomal or become chromosomally integrated, as long as it can be expressed to produce the desired polypeptide. Such vectors can be constructed by recombinant DNA technology methods that are well known and standard in the art. Vectors encoding the domain intrabody of interest can be plasmid, viral, or others known in the art, used for replication and expression in mammalian cells.

A wide variety of viral and non-viral vectors for delivery of a polynucleotide encoding a bi-functional polypeptide of the present disclosure are known in the art and may be employed in making the products and practicing the methods described herein. Vectors include, for example, eukaryotic expression vectors, including but not limited to viral expression vectors such as those derived from the class of retroviruses, adenoviruses or adeno-associated viruses.

Various vector systems are known to those skilled in the art and can be used to transfer the compositions of the invention into cells, e.g., encapsulation in liposomes, microparticles, microcapsules, recombinant cells capable of expressing the composition, construction of a nucleic acid as part of a retroviral, adenoviral, adeno-associated viral or other vector, injection of DNA, electroporation, calcium phosphate mediated transfection, etc.

Devices and Kits for Therapy

Pharmaceutical compositions that include the bi-functional polypeptide described herein can be administered with a medical device. The device can be designed with features such as portability, room temperature storage, and ease of use so that it can be used in emergency situations, e.g., by an untrained subject or by emergency personnel in the field, removed from medical facilities and other medical equipment. The device can include, e.g., one or more housings for storing pharmaceutical preparations that include a bi-functional polypeptide, and can be configured to deliver one or more unit doses of the antibody. The device can be further configured to administer a second agent, e.g., a neuroprotective agent, either as a single pharmaceutical composition that also includes the bi-functional polypeptide or as two separate pharmaceutical compositions.

A bi-functional polypeptide can be provided in a kit. In one embodiment, the kit includes (a) a container that contains a composition that includes a bi-functional polypeptide as described herein, and optionally (b) informational material. The informational material can be descriptive, instructional, marketing or other material that relates to the methods described herein and/or the use of the agents for therapeutic benefit.

In an embodiment, the kit also includes a second agent for treating a disorder described herein. For example, the kit includes a first container that contains a composition that includes the bi-functional polypeptide, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the bi-functional polypeptide, e.g., in a suitable dose, dosage form, or mode of administration (e.g., a dose, dosage form, or mode of administration described herein), to treat a subject who has had or who is at risk for a tauopathy described herein. The information can be provided in a variety of formats, include printed text, computer readable material, video recording, or audio recording, or information that provides a link or address to substantive material, e.g., on the internet.

In addition to the bi-functional polypeptide, the composition in the kit can include other ingredients, such as a solvent or buffer, a stabilizer, or a preservative. The bi-functional polypeptide can be provided in any form, e.g., liquid, dried or lyophilized form, preferably substantially pure and/or sterile. When the agents are provided in a liquid solution, the liquid solution preferably is an aqueous solution. In certain embodiments, the bi-functional polypeptide in the liquid solution is at a concentration of about 25 mg/mL to about 250 mg/mL (e.g., 40 mg/mL, 50 mg/mL, 60 mg/mL, 75 mg/mL, 85 mg/mL, 100 mg/mL, 125 mg/mL, 150 mg/mL, 200 mg/mL). When the bi-functional polypeptide is provided as a lyophilized product, the bi-functional polypeptide is at about 75 mg/vial to about 200 mg/vial (e.g., 100 mg/vial, 108.5 mg/vial, 125 mg/vial, 150 mg/vial). The lyophilized powder is generally reconstituted by the addition of a suitable solvent. The solvent, e.g., sterile water or buffer (e.g., PBS), can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the bi-functional polypeptide and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Bi-Functional Polypeptide

Exemplary single-chain bi-functional polypeptides comprising a first domain comprising an antigen binding domain of an antibody or functional fragment thereof which binds to an epitope of tau and a second domain comprising a proteasome-targeting PEST motif are provided below.

A bi-functional polypeptide comprises a first domain that is a single chain fragment (scFv) which binds to an epitope of tau, the scFv comprising a Tau specific $V_L$ domain ($V_L$ Tau) and a Tau specific $V_H$ domain ($V_H$ Tau).

The amino acid sequences for Tau specific V$_H$ domain (V$_H$ Tau) are provided in Table 2.

TABLE 2

Anti-tau scFV Heavy (V$_H$) domain sequences

| Sequence ID | (CDR sequence regions identified in BOLD) |
|---|---|
| A | QVQLQESGGGLVQPGRSLRLSCAASGFTFDDYAMHWVRQAPGKGLEW VAVISYDGSNKYYADSVKGRFTISRDNSKNTLYLQMNSLRAEDTAVYY CARDFAGAIAYWGQGTLVTVSS (SEQ ID NO: 1) |
| B | QVQLQQSGGGVVQPGRSLRLSCAASGFTFSSYGMHWVRQAPGKGLEW VAVISYDGSNKYYADSVKGRFTISRDNSKNTLYLQMNSLRAEDTAVYY CAKDLVGAKGNWGQGTLVTVSS (SEQ ID NO: 2) |
| C | QVQLQESGGGLVQPGRSLRLSCAASGFTFDDYAMHWVRQAPGKGLEW VAVISYDGSNKYYADSVKGRFTISRDNSKNTLYLQMNSLRAEDTAVYY CARDFAGAIAYWGQGTLVTVSS (SEQ ID NO: 3) |
| D | QVQLVESGGGLVKPGGSLRLSCAASGFTFSSYAMSWVRQAPGKGLEWV AAISGSGDNTYYADSVKGRFTISRDNSENTVHLQMAGLRAEDTALYFCA KDGPAVGNPQGYFDFWGRGTLVTVSS (SEQ ID NO: 4) |
| E | QVQLVQSGGGVVQPGRSLRLSCAASGFTFSSYGMHWVRQAPGKGLEW VASMSYDGNNKYYADSVKGRFTISRDNSKNTLYLQMNSLRAEDTAVYY CARDLRGALDYWGQGTLVTVSS (SEQ ID NO: 5) |
| F | QVQLVESGGGLVKPGGSLRLSCAASGFTFSDYYMSWIRQAPGKGLEWVS SISSSSSYIYVADSVKGRFTISRDNAKNSLYLQMNSLRAEDTAVYYCARD GIAARSGYYGMDVWGQGTLVTVSS (SEQ ID NO: 6) |
| G | QVQLQESGGGLVQPGRSLRLSCAASGFTFDDYAMHWVRQAPGKGLEW VAVISYDGSNKYVADSVKGRFTISRDNSKNTLYLQMNSLRAEDTAVYY CARDFAGAIAYWGQGTLVTVSS (SEQ ID NO: 7) |
| K | QVQLVESGGGLVKPGGSLRLSCAASGFTFSSYAMSWVRQAPGKGLEWV AAISGSGDNTYVADSVKGRFTISRDNSENTVHLQMAGLRAEDTALYFCA KDGPAVGNPQGYFDFWGRGTLVTVSS (SEQ ID NO: 8) |
| M | QVQLVQSGGGVVQPGRSLRLSCAASGFTFSSYGMHWVRQAPGKGLEW VAVISYDGSNKYVADSVKGRFTISRDNSKNTLYLQMNSLRAEDTAVYY CAKDLPDSNGYWGQGTLVTVSS (SEQ ID NO: 9) |
| N | QVQLVESGGGLVKPGGSLRLSCAASGFTFSSYAMSWVRQAPGKGLEWV AAISGSGDNTYVADSVKGRFTISRDNSENTVHLQMAGLRAEDTALYFCA KDGPAVGNPGGYFDFWGRGTLVTVSS (SEQ ID NO: 10) |
| O | QVQLVQSGGGVVHPGRSLRLSCAASGFTFSSYGMHWVRQAPGKGLEW VASMSYDGNNKYVADSVKGRFTTPRDNSKNTLYLQMNSLRAEDTAVY YCARDLRGALDYWGQGTLVTVSS (SEQ ID NO: 11) |
| Q | QVQLQESGGGLVQPGRSLRLSCAASGFTFDDYAMHWVRQAPGKGLEW VAVISYDGSNKYVADSVKGRFTISRDNSKNTLYLQMNSLRAEDTAVYY CARDFAGAIAYWGQGTLVTVSS (SEQ ID NO: 12) |
| S | QVQLQQSGGGVVQPGRSLRLSCAASGFTFSSYGMHWARQAPGKGLEW VAVISYDGSNKYVADSVKGRFTISRDNSKNTLYLQMNSLRAEDTAVYY CAKDLVGAKGNWAQGTLVTVSS (SEQ ID NO: 13) |
| T | QVQLQQSGGGVVQPGRSLRLSCAASGFTFSSYGMHWVRQAPGKGLEW VAVISYDGSNKYVADSVKGRFTISRDNSKNTLYLQMNSLRAEDTAVYY CAKDLVGAKGNWGQGTLVTVSS (SEQ ID NO: 14) |
| V | QVQLVESGGGLVKPGGSLRLSCAASGFTFSSYAMSWVRQAPGKGLEWV AAISGSGDNTYVADSVKGRFTISRDNSENTVHLQMAGLRAEDTALYFCA KDGPEVGNPGGYFDFWGRGTLVTVSS (SEQ ID NO: 15) |
| X | QVQLQQSGEGVVQPGRSLRLSCAASGFTFSSYGMHWVRQAPGKGLEWV AVISYDGSNKYVADSVKGRFTISRDNSKNTLYLQMNSLRAEDTAVYYC AKDLVGAKGNWGQGTLVTVSS (SEQ ID NO: 16) |
| Y | QVQLVQSGGGVVQPGRSLRLSCAASGFTFSSYGMHWVRQAPGKGLEW VASMSYDGDNKYVADSVKGRFTISRDNSKNTLYLQMNSLRAEDTAVYY CARDLRGALDYWGQGTLVTVSS (SEQ ID NO: 17) |

The amino acid sequences of Tau specific $V_L$ domain ($V_L$ Tau) are provided in Table 3.

TABLE 3

Anti-tau scFV Light ($V_L$) domain sequences

| scFV ID | (CDR sequence regions identified in BOLD) |
|---|---|
| A | EIVLTQSPSFLSASVGDRVTITCRASHGINNYLAWYQQKPGKAPKLLIYAASSLQSGVPSRFSGSGSGTDFTLTISSLQPEDFATYYCQQANSFPLTFGGGTK (SEQ ID NO: 18) |
| B | EIVLTQSPSTLSASVGERVTITCRASQSISSWLAWYQQKPGKAPKVLIYKASSLESGVPSRFSGSGSGTEFTLTISSLQPDDFATYYCQQYSTYLWTFGQGTK (SEQ ID NO: 19) |
| C | EIVLTQSPSILSASVGDRVTITCRASHGINNYLAWYQQKPGKAPKLLIYAASSLQSGVPSRFSGSGSGTDFTLTISSLQPEDFATYYCQQANSFPWTFGQGTK (SEQ ID NO: 20) |
| D | DIVMTQSPDSLAVSLGERATINCKSSQSLLYSSNNKDYLAWYQQKPGQSPRLLISWASTRESGVPDRFSGSGSGTDFTLTINRLQAEDVAVYYCQHYYSYPLTFGQGTK (SEQ ID NO: 21) |
| E | EIVLTQSPSTLSASIGDRVTITCRASQGISNYLAWYQQKPGKAPKLLIYAASTLQSGVPSRFSGSGSGTEFTLTISGLLPEDFASYFCQQASVFPVTFGGGTK (SEQ ID NO: 22) |
| F | EIVLTQSPSTLSASVGDRVTITCRASQSISSWLAWYQQKPGKAPKLLIYAASILQSGVPSRFSGSGSGTDFTLTISSLQPEDFATYYCLQDSNPYPLLTFGGGTK (SEQ ID NO: 23) |
| G | EIVLTQSPSFLSASVGDRVTITCRASHGINNYLAWYQQKPGKAPKLLIYAASSLQSGVPSRFSGSGSGTDFTLTISSLQPEDFATYYCQQANSFPLTFARTK (SEQ ID NO: 24) |
| K | DIVMTQSPDSLAVSLGERATINCKSSQSLLYSSNNKDYLAWYQQKPGQSPRLLISWASTRESGVPSRFSGSGSGTDFTLTINRLQAEDVAVYYCQHYYSYPLTFGQGTK (SEQ ID NO: 25) |
| M | DVVMTQSPSTLSASVGDRVTITCRASENINRWLAWYQQKPGKAPKLLIYKASSLESGVPSRCSGSGSGTEFTLTISSLQPDDFATYYCHQYTTYLWTFGQGTK (SEQ ID NO: 26) |
| N | DIVMTQSPDSLAVSLGERATINCKSSQSLLYSSNNKDYLAWYQQKPGQSPRLLIPWASTRESGVPDRFSGSGSGTDFTLTINRLQAEDVAVYYCQHYYSYPLTFGQGTK (SEQ ID NO: 27) |
| O | EIVLTQSPSTLSASIGDRVTITCRASQGISNYLAWYQQKPGKAPKLLIYAASTLQSGVPSRFSGSGSGTEFTLTISGLLPEDFASYFCQQASVFPVTFARTK (SEQ ID NO: 28) |
| Q | EICVTQSPSFLSASVGDRVTITCRASHGINNYLAWYQQKPGKAPKLLIYAASSLQSGVPSRFSGSGSGTDFTLTISSLQPEDFATYYCQQANSFPLTFGGGTK (SEQ ID NO: 29) |
| S | EIVLTQSPSTLSASVGERVTITCRASQSISSWLAWYQQKPGKAPKVLIYKASSLESGVPSRFSGSGSGTEFTLTISSLQPDDFATYYCQQYSTYLWTFGQGTK (SEQ ID NO: 30) |
| T | EIVLTQSPSTLSASVGERVTITCRASQSISSWLAWYQQKPGKAPKVLIYKASSLESGVPDRFSGSGSGTEFTLTISSLQPDDFATYYCQQYSTYLWTFGQGTK (SEQ ID NO: 31) |
| V | DIVMTKSPDSLAVSLGERATINCKSSQSLLYSSKNKDYLAWYQKKPGQSPRLLISWASTRESGVPDRFSGSGSGTDFTLTINRLQAEDVAVYYCQHYYSYPLTFGQGTK (SEQ ID NO: 32) |
| X | EIVLTQSPSTLSASVGERVTITCRASQSISSWLAWYQQKPGKAPKVLIYKASSLESGVPSRFSGSGSGTEFTLTISSLQPDDFATYYCQQYSTYLWTFGQGTK (SEQ ID NO: 33) |
| Y | EIVLTQSPSTLSASIGDRVTITCRASQGISNYLAWYQQKPGKAPKLLIYAASTLQSGVPSRFSGSGSGTEFTLTISGLLPEDFASYFCLQASVFPVTFGGGTK (SEQ ID NO: 34) |

The Tau specific V$_L$ domain (V$_L$ Tau) and a Tau specific V$_H$ domain (V$_H$ Tau) may be directly connected or linked via a polypeptide linker. For example, the Tau specific V$_L$ domain (V$_L$ Tau) and a Tau specific V$_H$ domain (V$_H$ Tau) are connected via a polypeptide linker that has an amino acid sequence that is at least 80%, at least 85%, at least 90%, at least 95%, at least 96%, at least 97%, at least 98%, at least 99% or 100% identical to an amino acid set forth in SEQ ID NO: 35 (GGGGSGGGGSGGGGS) or SEQ ID NO: 37 (YPYDVPDYA).

Amino Acid Sequence of HA Epitope:

YPYDVPDYA. (SEQ ID NO: 37)

The amino acid sequences for bi-functional polypeptides comprising an anti-Tau binding domain and a murine derived PEST domain are provided in Table 4.

TABLE 4

Anti-tau_mPEST bi-functional polypeptide amino acid sequences

| Intrabody ID | (HA epitope sequence region identified in BOLD; murine PEST sequence region identified in UNDERLINE) |
|---|---|
| A_Anti-Tau-mPEST | QVQLQESGGGLVQPGRSLRLSCAASGFTFDDYAMHWVRQAPGKGLE WVAVISYDGSNKYYADSVKGRFTISRDNSKNTLYLQMNSLRAEDTAV YYCARDFAGAIAYWGQGTLVTVSSGGGGSGGGGSGGGGSEIVLTQSP SFLSASVGDRVTITCRASHGINNYLAWYQQKPGKAPKLLIYAASSLQS GVPSRFSGSGSGTDFTLTISSLQPEDFATYYCQQANSFPLTFGGGTKYP YDVPDYASHGFPPEVEEQDDGTLPMSCAQESGMDRHPAACASARINV (SEQ ID NO: 40) |
| B Anti-Tau-mPEST | QVQLQQSGGGVVQPGRSLRLSCAASGFTFSSYGMHWVRQAPGKGLE WVAVISYDGSNKYYADSVKGRFTISRDNSKNTLYLQMNSLRAEDTAV YYCAKDLVGAKGNWGQGTLVTVSSGGGGSGGGGSGGGGSEIVLTQS PSTLSASVGERVTITCRASQSISSWLAWYQQKPGKAPKVLIYKASSLES GVPSRFSGSGSGTEFTLTISSLQPDDFATYYCQQYSTYLWTFGQGTKYP YDVPDYASHGFPPEVEEQDDGTLPMSCAQESGMDRHPAACASARINV (SEQ ID NO: 41) |
| C Anti-Tau-mPEST | QVQLQESGGGLVQPGRSLRLSCAASGFTFDDYAMHWVRQAPGKGLE WVAVISYDGSNKYYADSVKGRFTISRDNSKNTLYLQMNSLRAEDTAV YYCARDFAGAIAYWGQGTLVTVSSGGGGSGGGGSGGGGSEIVLTQSP SILSASVGDRVTITCRASHGINNYLAWYQQKPGKAPKLLIYAASSLQSG VPSRFSGSGSGTDFTLTISSLQPEDFATYYCQQANSFPWTFGQGTKYPY DVPDYASHGFPPEVEEQDDGTLPMSCAQESGMDRHPAACASARINV (SEQ ID NO: 42) |
| D Anti-Tau-mPEST | QVQLVESGGGLVKPGGSLRLSCAASGFTFSSYAMSWVRQAPGKGLEW VAAISGSGDNTYYADSVKGRFTISRDNSENTVHLQMAGLRAEDTALY FCAKDGPAVGNPQGYFDFWGRGTLVTVSSGGGGSGGGGSGGGGSDIV MTQSPDSLAVSLGERATINCKSSQSLLYSSNNKDYLAWYQQKPGQSPR LLISWASTRESGVPDRFSGSGSGTDFTLTINRLQAEDVAVYYCQHYYS YPLTFGQGTKYPYDVPDYASHGFPPEVEEQDDGTLPMSCAQESGMDR HPAACASARINV (SEQ ID NO: 43) |
| E Anti-Tau-mPEST | QVQLVQSGGGVVQPGRSLRLSCAASGFTFSSYGMHWVRQAPGKGLE WVASMSYDGNNKYYADSVKGRFTISRDNSKNTLYLQMNSLRAEDTA VYYCARDLRGALDYWGQGTLVTVSSGGGGSGGGGSGGGGSEIVLTQ SPSTLSASIGDRVTITCRASQGISNYLAWYQQKPGKAPKLLIYAASTLQ SGVPSRFSGSGSGTEFTLTISGLLPEDFASYFCQQASVFPVTFGGGTKYP YDVPDYASHGFPPEVEEQDDGTLPMSCAQESGMDRHPAACASARINV (SEQ ID NO: 44) |
| F Anti-Tau-mPEST | QVQLVESGGGLVKPGGSLRLSCAASGFTFSDYYMSWIRQAPGKGLEW VSSISSSSSYIYYADSVKGRFTISRDNAKNSLYLQMNSLRAEDTAVYYC ARDGIAARSGYYGMDVWGQGTLVTVSSGGGGSGGGGSGGGGSEIVL TQSPSTLSASVGDRVTITCRASQSISSWLAWYQQKPGKAPKLLIYAASI LQSGVPSRFSGSGSGTDFTLTISSLQPEDFATYYCLQDSNPYPLLTFGGG TKYPYDVPDYASHGFPPEVEEQDDGTLPMSCAQESGMDRHPAACASA RINV (SEQ ID NO: 45) |
| G Anti-Tau-mPEST | QVQLQESGGGLVQPGRSLRLSCAASGFTFDDYAMHWVRQAPGKGLE WVAVISYDGSNKYYADSVKGRFTISRDNSKNTLYLQMNSLRAEDTAV YYCARDFAGAIAYWGQGTLVTVSSGGGGSGGGGSGGGGSEIVLTQSP SFLSASVGDRVTITCRASHGINNYLAWYQQKPGKAPKLLIYAASSLQS GVPSRFSGSGSGTDFTLTISSLQPEDFATYYCQQANSFPLTFARTKYPY DVPDYASHGFPPEVEEQDDGTLPMSCAQESGMDRHPAACASARINV (SEQ ID NO: 46) |
| K Anti-Tau-mPEST | QVQLVESGGGLVKPGGSLRLSCAASGFTFSSYAMSWVRQAPGKGLEW VAAISGSGDNTYYADSVKGRFTISRDNSENTVHLQMAGLRAEDTALY FCAKDGPAVGNPQGYFDFWGRGTLVTVSSGGGGSGGGGSGGGGSDIV MTQSPDSLAVSLGERATINCKSSQSLLYSSNNKDYLAWYQQKPGQSPR LLISWASTRESGVPSRFSGSGSGTDFTLTINRLQAEDVAVYYCQHYYSY PLTFGQGTKYPYDVPDYASHGFPPEVEEQDDGTLPMSCAQESGMDRH PAACASARINV (SEQ ID NO: 47) |

TABLE 4-continued

Anti-tau_mPEST bi-functional polypeptide amino acid sequences

| Intrabody ID | (HA epitope sequence region identified in BOLD; murine PEST sequence region identified in UNDERLINE) |
|---|---|
| M Anti-Tau-mPEST | QVQLVQSGGGVVQPGRSLRLSCAASGFTFSSYGMHWVRQAPGKGLE WVAVISYDGSNKYYADSVKGRFTISRDNSKNTLYLQMNSLRAEDTAV YYCAKDLPDSNGYWGQGTLVTVSSGGGGSGGGGSGGGGSDVVMTQS PSTLSASVGDRVTITCRASENINRWLAWYQQKPGKAPKLLIYKASSLES GVPSRCSGSGSGTEFTLTISSLQPDDFATYYCHQYTTYLWTFGQGTKYPYDVPDYASHGFPPEVEEQDDGTLPMSCAQESGMDRHPAACASARIN V (SEQ ID NO: 48) |
| N Anti-Tau-mPEST | QVQLVESGGGLVKPGGSLRLSCAASGFTFSSYAMSWVRQAPGKGLEW VAAISGSGDNTYYADSVKGRFTISRDNSENTVHLQMAGLRAEDTALY FCAKDGPAVGNPGGYFDFWGRGTLVTVSSGGGGSGGGGSGGGGSDI VMTQSPDSLAVSLGERATINCKSSQSLLYSSNNKDYLAWYQQKPGQSPR LLIPWASTRESGVPDRFSGSGSGTDFTLTINRLQAEDVAVYYCQHYYS YPLTFGQGTKYPYDVPDYASHGFPPEVEEQDDGTLPMSCAQESGMDR HPAACASARINV (SEQ ID NO: 49) |
| O Anti-Tau-mPEST | QVQLVQSGGGVVHPGRSLRLSCAASGFTFSSYGMHWVRQAPGKGLE WVASMSYDGNNKYYADSVKGRFTTPRDNSKNTLYLQMNSLRAEDTA VYYCARDLRGALDYWGQGTLVTVSSGGGGSGGGGSGGGGSEIVLTQ SPSTLSASIGDRVTITCRASQGISNYLAWYQQKPGKAPKLLIYAASTLQ SGVPSRFSGSGSGTEFTLTISGLLPEDFASYFCQQASVFPVTFARTKYPY DVPDYASHGFPPEVEEQDDGTLPMSCAQESGMDRHPAACASARINV (SEQ ID NO: 50) |
| Q Anti-Tau-mPEST | QVQLQESGGGLVQPGRSLRLSCAASGFTFDDYAMHWVRQAPGKGLE WVAVISYDGSNKYYADSVKGRFTISRDNSKNTLYLQMNSLRAEDTAV YYCARDFAGAIAYWGQGTLVTVSSGGGGSGGGGSGGGGSEICVTQSP SFLSASVGDRVTITCRASHGINNYLAWYQQKPGKAPKLLIYAASSLQS GVPSRFSGSGSGTDFTLTISSLQPEDFATYYCQQANSFPLTFGGGTKYP YDVPDYASHGFPPEVEEQDDGTLPMSCAQESGMDRHPAACASARINV (SEQ ID NO: 51) |
| S Anti-Tau-mPEST | QVQLQQSGGGVVQPGRSLRLSCAASGFTFSSYGMHWARQAPGKGLE WVAVISYDGSNKYYADSVKGRFTISRDNSKNTLYLQMNSLRAEDTAV YYCAKDLVGAKGNWAQGTLVTVSSGGGGSGGGGSGGGGSEIVLTQS PSTLSASVGERVTITCRASQSISSWLAWYQQKPGKAPKVLIYKASSLES GVPSRFSGSGSGTEFTLTISSLQPDDFATYYCQQYSTYLWTFGQGTKYP YDVPDYASHGFPPEVEEQDDGTLPMSCAQESGMDRHPAACASARINV (SEQ ID NO: 52) |
| T Anti-Tau-mPEST | QVQLQQSGGGVVQPGRSLRLSCAASGFTFSSYGMHWVRQAPGKGLE WVAVISYDGSNKYYADSVKGRFTISRDNSKNTLYLQMNSLRAEDTAV YYCAKDLVGAKGNWGQGTLVTVSSGGGGSGGGGSGGGGSEIVLTQS PSTLSASVGERVTITCRASQSISSWLAWYQQKPGKAPKVLIYKASSLES GVPDRFSGSGSGTEFTLTISSLQPDDFATYYCQQYSTYLWTFGQGTKYPYDVPDYASHGFPPEVEEQDDGTLPMSCAQESGMDRHPAACASARIN V (SEQ ID NO: 53) |
| V Anti-Tau-mPEST | QVQLVESGGGLVKPGGSLRLSCAASGFTFSSYAMSWVRQAPGKGLEW VAAISGSGDNTYYADSVKGRFTISRDNSENTVHLQMAGLRAEDTALY FCAKDGPEVGNPGGYFDFWG?RGTLVTVSSGGGGSGGGGSGGGSDI VMTKSPDSLAVSLGERATINCKSSQSLLYSSKNKDYLAWYQQKPGQSP RLLISWASTRESGVPDRFSGSGSGTDFTLTINRLQAEDVAVYYCQHYY SYPLTFGQGTKYPYDVPDYASHGFPPEVEEQDDGTLPMSCAQESGMD RHPAACASARINV (SEQ ID NO: 54) |
| X Anti-Tau-mPEST | QVQLQQSGEGVVQPGRSLRLSCAASGFTFSSYGMHWVRQAPGKGLE WVAVISYDGSNKYYADSVKGRFTISRDNSKNTLYLQMNSLRAEDTAV YYCAKDLVGAKGNWGQGTLVTVSSGGGGSGGGGSGGGGSEIVLTQS PSTLSASVGERVTITCRASQSISSWLAWYQQKPGKAPKVLIYKASSLES GVPSFRSGSGSGTEFTLTISSLQPDDFATYYCQQYSTYLWTFGQGTKYP YDVPDYASHGFPPEVEEQDDGTLPMSCAQESGMDRHPAACASARINV (SEQ ID NO: 55) |
| Y Anti-Tau-mPEST | QVQLVQSGGGVVQPGRSLRLSCAASGFTFSSYGMHWVRQAPGKGLE WVASMSYDGDNKYYADSVKGRFTISRDNSKNTLYLQMNSLRAEDTA VYYCARDLRGALDYWGQGTLVTVSSGGGGSGGGGSGGGGSEIVLTQ SPSTLSASIGDRVTITCRASQGISNYLAWYQQKPGKAPKLLIYAASTLQ SGVPSRFSGSGSGTEFTLTISGLLPEDFASYFCLQASVFPVTFGGGTKYP YDVPDYASHGFPPEVEEQDDGTLPMSCAQESGMDRHPAACASARINV (SEQ ID NO: 56) |

The amino acid sequences for exemplary bi-functional polypeptides comprising an anti-Tau binding domain and a murine derived PEST domain are provided in Table 5.

TABLE 5

Anti-tau hPEST bi-functional polypeptide amino acid sequences

| Intrabody ID | (HA epitope sequence region identified in BOLD; murine PEST sequence region identified in UNDERLINE) |
|---|---|
| A Anti-Tau-hPEST | QVQLQESGGGLVQPGRSLRLSCAASGFTFDDYAMHWVRQAPGKGLE WVAVISYDGSNKYYADSVKGRFTISRDNSKNTLYLQMNSLRAEDTAV YYCARDFAGAIAYWGQGTLVTVSSGGGGSGGGGSGGGGSEIVLTQSP SFLSASVGDRVTITCRASHGINNYLAWYQQKPGKAPKLLIYAASSLQS GVPSRFSGSGSGTDFTLTISSLQPEDFATYYCQQANSFPLTFGGGTKYP YDVPDYANPDFPPEVEEQDASTLPVSCAWESGMKRHRAACASASINV (SEQ ID NO: 57) |
| B Anti-Tau-hPEST | QVQLQQSGGGVVQPGRSLRLSCAASGFTFSSYGMHWVRQAPGKGLE WVAVISYDGSNKYYADSVKGRFTISRDNSKNTLYLQMNSLRAEDTAV YYCAKDLVGAKGNWGQGTLVTVSSGGGGSGGGGSGGGGSEIVLTQS PSTLSASVGERVTITCRASQSISSWLAWYQQKPGKAPKVLIYKASSLES GVPSRFSGSGSGTEFTLTISSLQPDDFATYYCQQYSTYLWTFGQGTKYP YDVPDYANPDFPPEVEEQDASTLPVSCAWESGMKRHRAACASASINV (SEQ ID NO: 58) |
| C Anti-Tau-hPEST | QVQLQESGGGLVQPGRSLRLSCAASGFTFDDYAMHWVRQAPGKGLE WVAVISYDGSNKYYADSVKGRFTISRDNSKNTLYLQMNSLRAEDTAV YYCARDFAGAIAYWGQGTLVTVSSGGGGSGGGGSGGGGSEIVLTQSP SILSASVGDRVTITCRASHGINNYLAWYQQKPGKAPKLLIYAASSLQSG VPSRFSGSGSGTDFTLTISSLQPEDFATYYCQQANSFPWTFGQGTKYPY DVPDYANPDFPPEVEEQDASTLPVSCAWESGMKRHRAACASASINV (SEQ ID NO: 59) |
| D Anti-Tau-hPEST | QVQLVESGGGLVKPGGSLRLSCAASGFTFSSYAMSWVRQAPGKGLEW VAAISGSGDNTYYADSVKGRFTISRDNSENTVHLQMAGLRAEDTALY FCAKDGPAVGNPQGYFDFWGRGTLVTVSSGGGGSGGGGSGGGGSDIV MTQSPDSLAVSLGERATINCKSSQSLLYSSNNKDYLAWYQQKPGQSPR LLISWASTRESGVPDRFSGSGSGTDFTLTINRLQAEDVAVYYCQHYYS YPLTFGQGTKYPYDVPDYANPDFPPEVEEQDASTLPVSCAWESGMKR HRAACASASINV (SEQ ID NO: 60) |
| E Anti-Tau-hPEST | QVQLVQSGGGVVQPGRSLRLSCAASGFTFSSYGMHWVRQAPGKGLE WVASMSYDGNNKYYADSVKGRFTISRDNSKNTLYLQMNSLRAEDTA VYYCARDLRGALDYWGQGTLVTVSSGGGGSGGGGSGGGGSEIVLTQ SPSTLSASIGDRVTITCRASQGISNYLAWYQQKPGKAPKLLIYAASTLQ SGVPSRFSGSGSGTEFTLTISGLLPEDFASYFCQQASVFPVTFGGGTKYP YDVPDYANPDFPPEVEEQDASTLPVSCAWESGMKRHRAACASASINV (SEQ ID NO: 61) |
| F Anti-Tau-hPEST | QVQLVESGGGLVKPGGSLRLSCAASGFTFSDYYMSWIRQAPGKGLEW VSSISSSSSYIYYADSVKGRFTISRDNAKNSLYLQMNSLRAEDTAVYYC ARDGIAARSGYYGMDVWGQGTLVTVSSGGGGSGGGGSGGGGSEIVL TQSPSTLSASVGDRVTITCRASQSISSWLAWYQQKPGKAPKLLIYAASI LQSGVPSRFSGSGSGTDFTLTISSLQPEDFATYYCLQDSNPYPLLTFGGG TKYPYDVPDYANPDFPPEVEEQDASTLPVSCAWESGMKRHRAACASA SINV (SEQ ID NO: 62) |
| G Anti-Tau-hPEST | QVQLQESGGGLVQPGRSLRLSCAASGFTFDDYAMHWVRQAPGKGLE WVAVISYDGSNKYYADSVKGRFTISRDNSKNTLYLQMNSLRAEDTAV YYCARDFAGAIAYWGQGTLVTVSSGGGGSGGGGSGGGGSEIVLTQSP SFLSASVGDRVTITCRASHGINNYLAWYQQKPGKAPKLLIYAASSLQS GVPSRFSGSGSGTDFTLTISSLQPEDFATYYCQQANSFPLTFARTKYPY DVPDYANPDFPPEVEEQDASTLPVSCAWESGMKRHRAACASASINV (SEQ ID NO: 63) |
| K Anti-Tau-hPEST | QVQLVESGGGLVKPGGSLRLSCAASGFTFSSYAMSWVRQAPGKGLEW VAAISGSGDNTYYADSVKGRFTISRDNSENTVHLQMAGLRAEDTALY FCAKDGPAVGNPQGYFDFWGRGTLVTVSSGGGGSGGGGSGGGGSDIV MTQSPDSLAVSLGERATINCKSSQSLLYSSNNKDYLAWYQQKPGQSPR LLISWASTRESGVPSRFSGSGSGTDFTLTINRLQAEDVAVYYCQHYYSY PLTFGQGTKYPYDVPDYANPDFPPEVEEQDASTLPVSCAWESGMKRH RAACASASINV (SEQ ID NO: 64) |

TABLE 5-continued

Anti-tau hPEST bi-functional polypeptide amino acid sequences

| Intrabody ID | (HA epitope sequence region identified in BOLD; murine PEST sequence region identified in UNDERLINE) |
|---|---|
| M Anti-Tau-hPEST | QVQLVQSGGGVVQPGRSLRLSCAASGFTFSSYGMHWVRQAPGKGLE WVAVISYDGSNKYYADSVKGRFTISRDNSKNTLYLQMNSLRAEDTAV YYCAKDLPDSNGYWGQGTLVTVSSGGGGSGGGGSGGGGSDVVMTQS PSTLSASVGDRVTITCRASENINRWLAWYQQKPGKAPKLLIYKASSLES GVPSRCSGSGSGTEFTLTISSLQPDDFATYYCHQYTTYLWTFGQGTKY PYDVPDYANPDFPPEVEEQDASTLPVSCAWESGMKRHRAACASASIN V (SEQ ID NO: 65) |
| N Anti-Tau-hPEST | QVQLVESGGGLVKPGGSLRLSCAASGFTFSSYAMSWVRQAPGKGLEW VAAISGSGDNTYYADSVKGRFTISRDNSENTVHLQMAGLRAEDTALY FCAKDGPAVGNPGGYFDFWGRGTLVTVSSGGGGSGGGGSGGGGSDIV MTQSPDSLAVSLGERATINCKSSQSLLYSSNNKDYLAWYQQKPGQSPR LLIPWASTRESGVPDRFSGSGSGTDFTLTINRLQAEDVAVYYCQHYYS YPLTFGQGTKYPYDVPDYANPDFPPEVEEQDASTLPVSCAWESGMKR HRAACASASINV (SEQ ID NO: 66) |
| O Anti-Tau-hPEST | QVQLVQSGGGVVHPGRSLRLSCAASGFTFSSYGMHWVRQAPGKGLE WVASMSYDGNNKYYADSVKGRFTTPRDNSKNTLYLQMNSLRAEDTA VYYCARDLRGALDYWGQGTLVTVSSGGGGSGGGGSGGGGSEIVLTQ SPSTLSASIGDRVTITCRASQGISNYLAWYQQKPGKAPKLLIYAASTLQ SGVPSRFSGSGSGTEFTLTISGLLPEDFASYFCQQASVFPVTFARTKYPY DVPDYANPDFPPEVEEQDASTLPVSCAWESGMKRHRAACASASINV (SEQ ID NO: 67) |
| Q Anti-Tau-hPEST | QVQLQESGGGLVQPGRSLRLSCAASGFTFDDYAMHWVRQAPGKGLE WVAVISYDGSNKYYADSVKGRFTISRDNSKNTLYLQMNSLRAEDTAV YYCARDFAGAIAYWGQGTLVTVSSGGGGSGGGGSGGGGSEICVTQSP SFLSASVGDRVTITCRASHGINNYLAWYQQKPGKAPKLLIYAASSLQS GVPSRFSGSGSGTDFTLTISSLQPEDFATYYCQQANSFPLTFGGGTKYP YDVPDYANPDFPPEVEEQDASTLPVSCAWESGMKRHRAACASASINV (SEQ ID NO: 68) |
| S Anti-Tau-hPEST | QVQLQQSGGGVVQPGRSLRLSCAASGFTFSSYGMHWARQAPGKGLE WVAVISYDGSNKYYADSVKGRFTISRDNSKNTLYLQMNSLRAEDTAV YYCAKDLVGAKGNWAQGTLVTVSSGGGGSGGGGSGGGGSEIVLTQS PSTLSASVGERVTITCRASQSISSWLAWYQQKPGKAPKVLIYKASSLES GVPSRFSGSGSGTEFTLTISSLQPDDFATYYCQQYSTYLWTFGQGTKYP YDVPDYANPDFPPEVEEQDASTLPVSCAWESGMKRHRAACASASINV (SEQ ID NO: 69) |
| T Anti-Tau-hPEST | QVQLQQSGGGVVQPGRSLRLSCAASGFTFSSYGMHWVRQAPGKGLE WVAVISYDGSNKYYADSVKGRFTISRDNSKNTLYLQMNSLRAEDTAV YYCAKDLVGAKGNWGQGTLVTVSSGGGGSGGGGSGGGGSEIVLTQS PSTLSASVGERVTITCRASQSISSWLAWYQQKPGKAPKVLIYKASSLES GVPDRFSGSGSGTEFTLTISSLQPDDFATYYCQQYSTYLWTFGQGTKY PYDVPDYANPDFPPEVEEQDASTLPVSCAWESGMKRHRAACASASIN V (SEQ ID NO: 70) |
| V Anti-Tau-hPEST | QVQLVESGGGLVKPGGSLRLSCAASGFTFSSYAMSWVRQAPGKGLEW VAAISGSGDNTYYADSVKGRFTISRDNSENTVHLQMAGLRAEDTALY FCAKDGPEVGNPGGYFDFWGRGTLVTVSSGGGGSGGGGSGGGGSDIV MTKSPDSLAVSLGERATINCKSSQSLLYSSKNKDYLAWYQQKPGQSPR LLISWASTRESGVPDRFSGSGSGTDFTLTINRLQAEDVAVYYCQHYYS YPLTFGQGTKYPYDVPDYANPDFPPEVEEQDASTLPVSCAWESGMKR HRAACASASINV (SEQ ID NO: 71) |
| X Anti-Tau-hPEST | QVQLQQSGEGVVQPGRSLRLSCAASGFTFSSYGMHWVRQAPGKGLE WVAVISYDGSNKYYADSVKGRFTISRDNSKNTLYLQMNSLRAEDTAV YYCAKDLVGAKGNWGQGTLVTVSSGGGGSGGGGSGGGGSEIVLTQS PSTLSASVGERVTITCRASQSISSWLAWYQQKPGKAPKVLIYKASSLES GVPSFRSGSGSGTEFTLTISSLQPDDFATYYCQQYSTYLWTFGQGTKYP YDVPDYANPDFPPEVEEQDASTLPVSCAWESGMKRHRAACASASINV (SEQ ID NO: 72) |
| Y Anti-Tau-hPEST | QVQLVQSGGGVVQPGRSLRLSCAASGFTFSSYGMHWVRQAPGKGLE WVASMSYDGDNKYYADSVKGRFTISRDNSKNTLYLQMNSLRAEDTA VYYCARDLRGALDYWGQGTLVTVSSGGGGSGGGGSGGGGSEIVLTQ SPSTLSASIGDRVTITCRASQGISNYLAWYQQKPGKAPKLLIYAASTLQ SGVPSRFSGSGSGTEFTLTISGLLPEDFASYFCLQASVFPVTFGGGTKYP YDVPDYANPDFPPEVEEQDASTLPVSCAWESGMKRHRAACASASINV (SEQ ID NO: 73) |

Example 2

Figure 3:
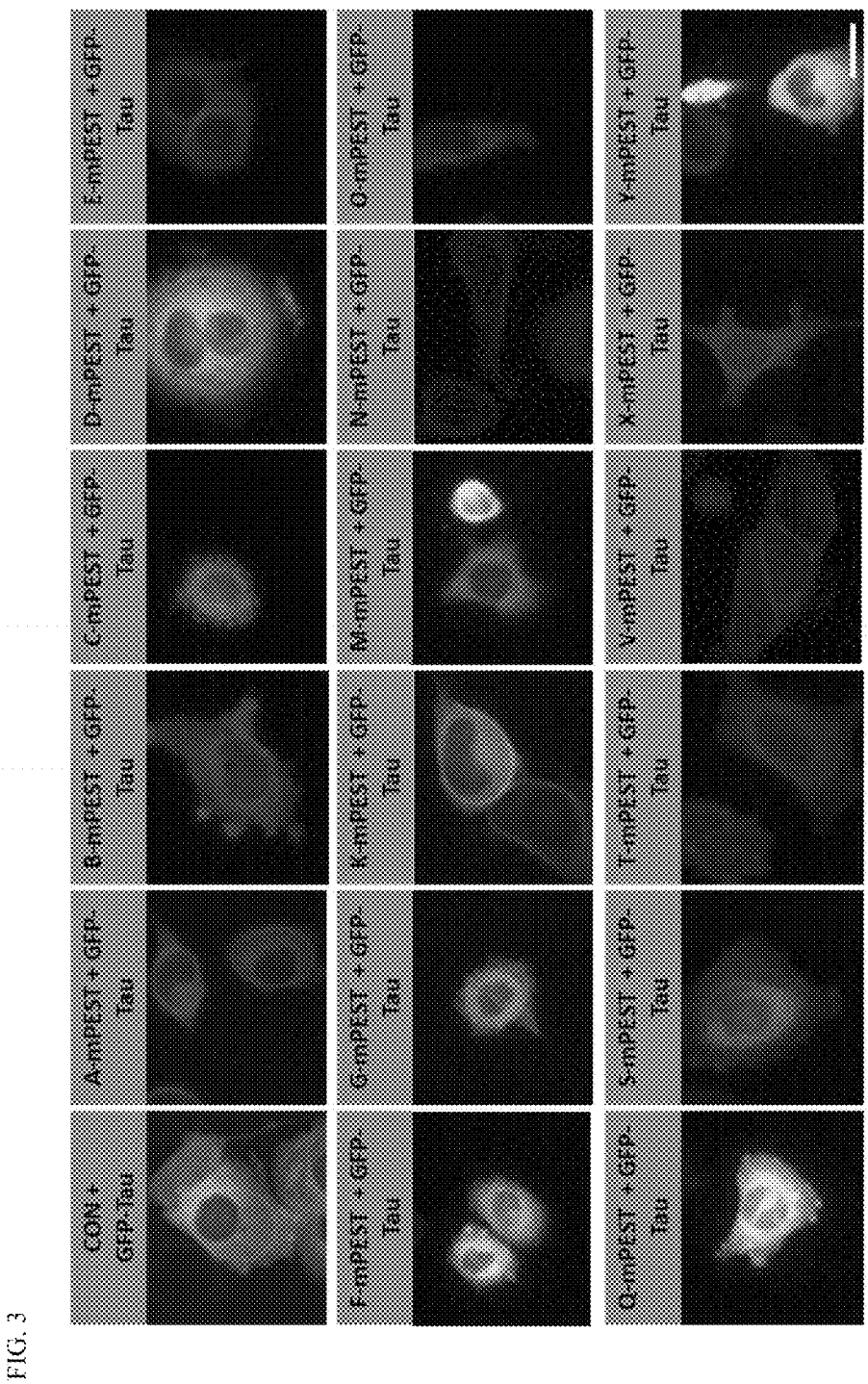
FIG. 3 depicts representative live cell images of tau-GFP expressing ST14A cells 48 hours post transfection control (CON+GFP-tau; empty pcDNA3.1 plasmid) or anti-Tau-PEST bi-functional polypeptides according to the present disclosure. Images were taken at 32× magnification for each sample and then zoomed in digitally to cell level (Scale bar 20 μm).
Figure 4:
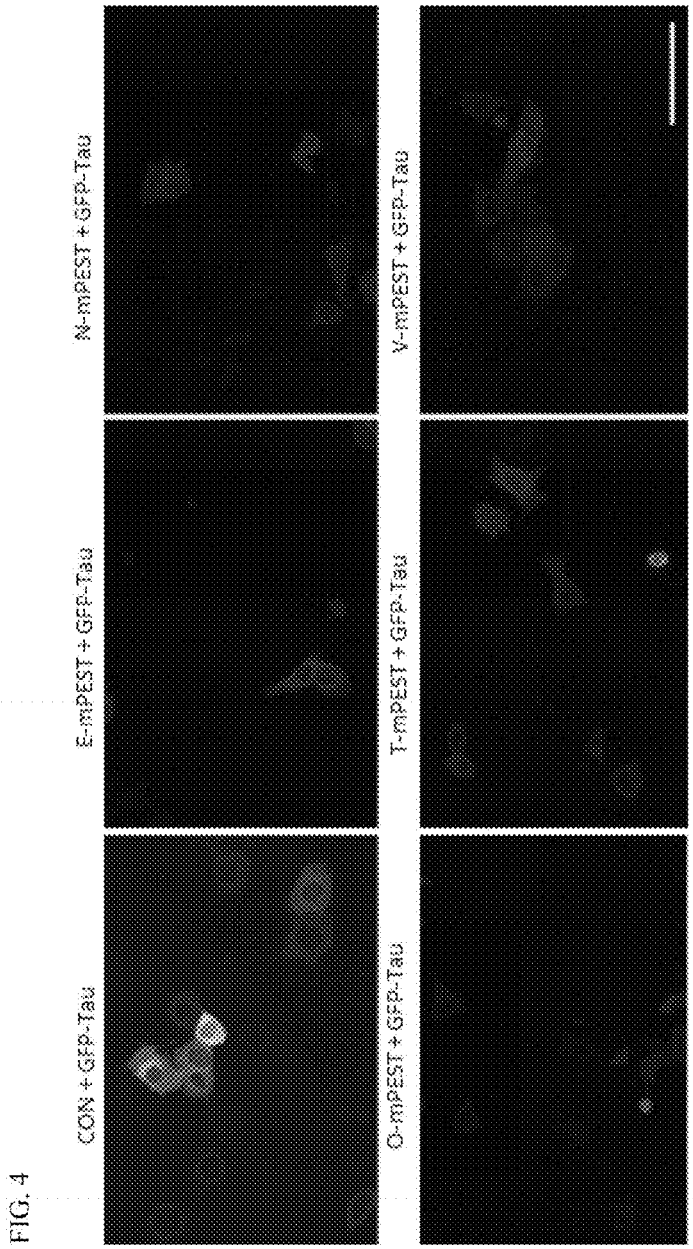
FIG. 4 depicts representative live cell images of tau-GFP expressing ST14A cells 48 hours post transfection control (CON+GFP-tau; empty pcDNA3.1 plasmid) or anti-Tau-PEST bi-functional polypeptides according to the present disclosure. Images were taken at 32× magnification for each sample (Scale bar 50 μm).

Anti-Tau-mousePEST (mPEST) intrabodies were screened in the ST14A cell line that was previously described in detail (Ehrlich, M. E., et. al., ST14A Cells Have Properties of a Medium-Size Spiny Neuron, *Experimental Neurology*, Volume 167, Issue 2, 2001, Pages 215-226) Cells were propagated at the permissive temperature of 33° C. in Dulbecco's modified Eagle medium (Life Technologies, Bethesda, MD) supplemented with 0.11 g/liter sodium pyruvate, 3.7 g/liter sodium bicarbonate, 0.29 g/liter glutamine, 3.9 g/liter Hepes, 100 units/ml penicillin—streptomycin (Life Technologies), plus 10% fetal calf serum. Anti-tau-mPEST intrabodies were subcloned into pcDNA3.1- and co-transfected with pTetO-FUW-GFP-Tau (2N4R) and rtTA. A flexible (G45)4 linker was placed between GFP and Tau to allow independent folding of the two proteins. 4 hours after transfection, PEI transfection reagent was aspirated off of cells, and media was replaced with ST14A media supplemented with 2000 ng/mL doxycycline to induce maximal GFP-Tau expression. 48H after transfection, cells were imaged for GFP-tau fluorescence at 32× magnification (FIG. 3) and at 50 magnification (FIG. 4) An n of 2 was performed for each intrabody. Reductions in GFP mean fluorescence intensity correspond to reductions of the fused protein.

Live cell imaging of transfected cells revealed that without anti-Tau intrabodies (see CON+GFP-Tau; empty pcDNA3.1 plasmid), GFP remained diffuse throughout the cells. In cells co-transfected with anti-Tau-mPEST intrabodies resulted in a dramatic reduction of observable GFP fluorescence. See, for example, FIG. 3 and FIG. 4 which demonstrate a dramatic reduction of observable GFP fluorescence in cells co-transfected with anti-Tau-mPEST intrabodies E-mPEST+GFP-Tau, N-mPEST+GFP-Tau, O-mPEST+GFP-Tau, T-mPEST+GFP-Tau, V-mPEST+GFP-Tau, and X-mPEST+GFP-Tau.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An anti-tau bi-functional polypeptide, comprising a polypeptide having an amino acid sequence at least 90% identical to a sequence selected from the group consisting of SEQ ID NO: 57, SEQ ID NO: 61, SEQ ID NO: 62, SEQ ID NO: 65, SEQ ID NO: 66, SEQ ID NO: 67, SEQ ID NO: 69, SEQ ID NO: 70, SEQ ID NO: 71, and SEQ ID NO: 72, wherein percent identity is determined using the BLASTP algorithm.

2. A bi-functional polypeptide, comprising
(a) a first domain of an intrabody which binds to an epitope of Tau wherein the intrabody is an antibody fragment (scFv) including a Tau specific VL immunoglobulin domain (VL Tau) and a Tau specific VH immunoglobulin domain (VH Tau) connected by a first linker, wherein the first linker is at least 90% identical to the amino acid sequence as set forth in SEQ ID NO: 35;
(b) a second domain comprising a proteasome-targeting PEST motif having an amino acid sequence at least 90% identical to the amino acid sequence as set forth in SEQ ID NO: 38 or SEQ ID NO: 39;
wherein percent identity is determined using the BLASTP algorithm.

3. The polypeptide of claim 2, wherein the second domain is at least 90% identical to the amino acid sequence as set forth in SEQ ID NO: 38.

4. The polypeptide of claim 2, wherein the second domain is at least 90% identical to the amino acid sequence as set forth in SEQ ID NO: 39.

5. The polypeptide of claim 2, wherein the first domain and the second domain are connected by a second linker.

6. The polypeptide of claim 5, wherein the second linker is at least 90% identical to the amino acid sequence as set forth in SEQ ID NO: 37.

7. The polypeptide of claim 2, wherein the domains are arranged in the order of $V_L$Tau-linker-$V_H$Tau-PEST motif.

8. The polypeptide of claim 2, wherein the domains are arranged in the order of $V_H$Tau-linker-$V_L$Tau-PEST motif.

9. The bi-functional polypeptide of claim 2, wherein the $V_H$ Tau domain is at least 90% identical to an amino acid sequence as set forth in SEQ ID NO: 6; and wherein the $V_L$ Tau domain is at least 90% identical to an amino acid sequence as set forth in SEQ ID NO: 23.

10. The bi-functional polypeptide of claim 2, wherein the $V_H$ Tau domain is at least 90% identical to an amino acid sequence as set forth in SEQ ID NO: 15; and wherein the $V_L$ Tau domain is at least 90% identical to an amino acid sequence as set forth in SEQ ID NO: 32.

11. The bi-functional polypeptide of claim 2, wherein the $V_H$ Tau domain is at least 90% identical to an amino acid sequence as set forth in SEQ ID NO: 10; and wherein the $V_L$ Tau domain is at least 90% identical to an amino acid sequence as set forth in SEQ ID NO: 27.

12. The bi-functional polypeptide of claim 2, wherein the $V_H$ Tau domain is at least 90% identical to an amino acid sequence as set forth in SEQ ID NO: 1; and wherein the $V_L$ Tau domain is at least 90% identical to an amino acid sequence as set forth in SEQ ID NO: 18.

13. The bi-functional polypeptide of claim 2, wherein the $V_H$ Tau domain is at least 90% identical to an amino acid sequence as set forth in SEQ ID NO: 5; and wherein the $V_L$ Tau domain is at least 90% identical to an amino acid sequence as set forth in SEQ ID NO: 22.

14. The bi-functional polypeptide of claim 2, wherein the $V_H$ Tau domain is at least 90% identical to an amino acid sequence as set forth in SEQ ID NO: 9; and wherein the $V_L$ Tau domain is at least 90% identical to an amino acid sequence as set forth in SEQ ID NO: 26.

15. The bi-functional polypeptide of claim 2, wherein the $V_H$ Tau domain is at least 90% identical to an amino acid sequence as set forth in SEQ ID NO: 16; and wherein the $V_L$ Tau domain is at least 90% identical to an amino acid sequence as set forth in SEQ ID NO: 33.

16. The bi-functional polypeptide of claim 2, wherein the $V_H$ Tau domain is at least 90% identical to an amino acid sequence as set forth in SEQ ID NO: 14; and wherein the $V_L$ Tau domain is at least 90% identical to an amino acid sequence as set forth in SEQ ID NO: 31.

17. The bi-functional polypeptide of claim 2, wherein the $V_H$ Tau domain is at least 90% identical to an amino acid sequence as set forth in SEQ ID NO: 11; and wherein the $V_L$ Tau domain is at least 90% identical to an amino acid sequence as set forth in SEQ ID NO: 28.

18. The bi-functional polypeptide of claim 2, wherein the $V_H$ Tau domain is at least 90% identical to an amino acid sequence as set forth in SEQ ID NO: 13; and wherein the $V_L$ Tau domain is at least 90% identical to an amino acid sequence as set forth in SEQ ID NO: 30.

19. A composition comprising the bi-functional polypeptide of claim 2.

20. The composition of claim 19, further comprising a pharmaceutically acceptable carrier.

21. A method for the treatment of a tauopathy in a patient, which comprises administering to the patient in need of such treatment a therapeutically effective amount of the bi-functional polypeptide of claim 2.

22. The method of claim 21, wherein the tauopathy is selected from the group consisting of Alzheimer's Disease (AD), progressive supranuclear palsy (PSP), frontotemporal dementia with Parkinsonism on chromosome-17 (FTDP-17), corticobasal degeneration (CBD), Pick's disease, chronic traumatic encephalopathy (CTE), Lewy Body dementia, tuberous sclerosis, traumatic brain injury (TBI), Down syndrome, Guam parkinsonism dementia complex, Dementia pugilistica, Dementia with argyrophilic grains, Pallido-ponto-nigral degeneration, and Gerstmann-Straussler-Scheinker disease.

* * * * *

SEQUENCE LISTING

```
<160> NUMBER OF SEQ ID NOS: 73

<210> SEQ ID NO 1
<211> LENGTH: 117
<212> TYPE: PRT
<213> ORGANISM: Artificial Sequence
<220> FEATURE:
<223> OTHER INFORMATION: synthetic protein

<400> SEQUENCE: 1

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser
        115

<210> SEQ ID NO 2
<211> LENGTH: 117
<212> TYPE: PRT
<213> ORGANISM: Artificial Sequence
<220> FEATURE:
<223> OTHER INFORMATION: synthetic protein

<400> SEQUENCE: 2

Gln Val Gln Leu Gln Gln Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Val Gly Ala Lys Gly Asn Trp Gly Gln Gly Thr Leu
            100                 105                 110

Val Thr Val Ser Ser
            115
```

<210> SEQ ID NO 3
<211> LENGTH: 117
<212> TYPE: PRT
<213> ORGANISM: Artificial Sequence
<220> FEATURE:
<223> OTHER INFORMATION: synthetic protein

<400> SEQUENCE: 3

```
Gln Val Gln Leu Gln Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Phe Ala Gly Ala Ile Ala Tyr Trp Gly Gln Gly Thr Leu
            100                 105                 110

Val Thr Val Ser Ser
            115
```

<210> SEQ ID NO 4
<211> LENGTH: 123
<212> TYPE: PRT
<213> ORGANISM: Artificial Sequence
<220> FEATURE:
<223> OTHER INFORMATION: synthetic protein

<400> SEQUENCE: 4

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
 50                  55                  60

Lys Gly Arg Phe Thr Ile Ser Arg Asp Asn Ser Glu Asn Thr Val His
```

```
              65                  70                  75                  80
Leu Gln Met Ala Gly Leu Arg Ala Glu Asp Thr Ala Leu Tyr Phe Cys
                85                  90                  95

Ala Lys Asp Gly Pro Ala Val Gly Asn Pro Gln Gly Tyr Phe Asp Phe
            100                 105                 110

Trp Gly Arg Gly Thr Leu Val Thr Val Ser Ser
        115                 120
```

<210> SEQ ID NO 5
<211> LENGTH: 117
<212> TYPE: PRT
<213> ORGANISM: Artificial Sequence
<220> FEATURE:
<223> OTHER INFORMATION: synthetic protein

<400> SEQUENCE: 5

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ser Met Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Arg Gly Ala Leu Asp Tyr Trp Gly Gln Gly Thr Leu
            100                 105                 110

Val Thr Val Ser Ser
        115
```

<210> SEQ ID NO 6
<211> LENGTH: 123
<212> TYPE: PRT
<213> ORGANISM: Artificial Sequence
<220> FEATURE:
<223> OTHER INFORMATION: synthetic protein

<400> SEQUENCE: 6

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Ala Ala Arg Ser Gly Tyr Tyr Gly Met Asp Val
            100                 105                 110

Trp Gly Gln Gly Thr Leu Val Thr Val Ser Ser
        115                 120
```

<210> SEQ ID NO 7
<211> LENGTH: 117
<212> TYPE: PRT
<213> ORGANISM: Artificial Sequence
<220> FEATURE:
<223> OTHER INFORMATION: synthetic protein

<400> SEQUENCE: 7

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser
        115

<210> SEQ ID NO 8
<211> LENGTH: 123
<212> TYPE: PRT
<213> ORGANISM: Artificial Sequence
<220> FEATURE:
<223> OTHER INFORMATION: synthetic protein

<400> SEQUENCE: 8

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
        50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Ala Val Gly Asn Pro Gln Gly Tyr Phe Asp Phe
            100                 105                 110

Trp Gly Arg Gly Thr Leu Val Thr Val Ser Ser
        115                 120

<210> SEQ ID NO 9
<211> LENGTH: 117
<212> TYPE: PRT
<213> ORGANISM: Artificial Sequence
<220> FEATURE:
<223> OTHER INFORMATION: synthetic protein

<400> SEQUENCE: 9

Gln Val Gln Leu Val Gln Ser Gly Gly Gly Val Val Gln Pro Gly Arg

```
1               5                  10                  15
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Pro Asp Ser Asn Gly Tyr Trp Gly Gln Gly Thr Leu
                100                 105                 110

Val Thr Val Ser Ser
            115

<210> SEQ ID NO 10
<211> LENGTH: 123
<212> TYPE: PRT
<213> ORGANISM: Artificial Sequence
<220> FEATURE:
<223> OTHER INFORMATION: synthetic protein

<400> SEQUENCE: 10

Gln Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Ala Val Gly Asn Pro Gly Gly Tyr Phe Asp Phe
                100                 105                 110

Trp Gly Arg Gly Thr Leu Val Thr Val Ser Ser
            115                 120

<210> SEQ ID NO 11
<211> LENGTH: 117
<212> TYPE: PRT
<213> ORGANISM: Artificial Sequence
<220> FEATURE:
<223> OTHER INFORMATION: synthetic protein

<400> SEQUENCE: 11

Gln Val Gln Leu Val Gln Ser Gly Gly Gly Val Val His Pro Gly Arg
1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ser Met Ser Tyr Asp Gly Asn Asn Lys Tyr Tyr Ala Asp Ser Val
    50                  55                  60
```

```
Lys Gly Arg Phe Thr Thr Pro Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Arg Gly Ala Leu Asp Tyr Trp Gly Gln Gly Thr Leu
            100                 105                 110

Val Thr Val Ser Ser
            115

<210> SEQ ID NO 12
<211> LENGTH: 117
<212> TYPE: PRT
<213> ORGANISM: Artificial Sequence
<220> FEATURE:
<223> OTHER INFORMATION: synthetic protein

<400> SEQUENCE: 12

Gln Val Gln Leu Gln Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Phe Ala Gly Ala Ile Ala Tyr Trp Gly Gln Gly Thr Leu
            100                 105                 110

Val Thr Val Ser Ser
            115

<210> SEQ ID NO 13
<211> LENGTH: 117
<212> TYPE: PRT
<213> ORGANISM: Artificial Sequence
<220> FEATURE:
<223> OTHER INFORMATION: synthetic protein

<400> SEQUENCE: 13

Gln Val Gln Leu Gln Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Ala Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Val Gly Ala Lys Gly Asn Trp Ala Gln Gly Thr Leu
            100                 105                 110

Val Thr Val Ser Ser
            115
```

```
<210> SEQ ID NO 14
<211> LENGTH: 117
<212> TYPE: PRT
<213> ORGANISM: Artificial Sequence
<220> FEATURE:
<223> OTHER INFORMATION: synthetic protein

<400> SEQUENCE: 14

Gln Val Gln Leu Gln Gln Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Gly Gln Gly Thr Leu
            100                 105                 110

Val Thr Val Ser Ser
        115

<210> SEQ ID NO 15
<211> LENGTH: 123
<212> TYPE: PRT
<213> ORGANISM: Artificial Sequence
<220> FEATURE:
<223> OTHER INFORMATION: synthetic protein

<400> SEQUENCE: 15

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
        50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Glu Val Gly Asn Pro Gly Gly Tyr Phe Asp Phe
            100                 105                 110

Trp Gly Arg Gly Thr Leu Val Thr Val Ser Ser
        115                 120

<210> SEQ ID NO 16
<211> LENGTH: 117
<212> TYPE: PRT
<213> ORGANISM: Artificial Sequence
<220> FEATURE:
<223> OTHER INFORMATION: synthetic protein

<400> SEQUENCE: 16
```

```
Gln Val Gln Leu Gln Gln Ser Gly Glu Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Gly Gln Gly Thr Leu
            100                 105                 110

Val Thr Val Ser Ser
            115
```

<210> SEQ ID NO 17
<211> LENGTH: 117
<212> TYPE: PRT
<213> ORGANISM: Artificial Sequence
<220> FEATURE:
<223> OTHER INFORMATION: synthetic protein

<400> SEQUENCE: 17

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ser Met Ser Tyr Asp Gly Asp Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Arg Gly Ala Leu Asp Tyr Trp Gly Gln Gly Thr Leu
            100                 105                 110

Val Thr Val Ser Ser
            115
```

<210> SEQ ID NO 18
<211> LENGTH: 103
<212> TYPE: PRT
<213> ORGANISM: Artificial Sequence
<220> FEATURE:
<223> OTHER INFORMATION: synthetic protein

<400> SEQUENCE: 18

```
Glu Ile Val Leu Thr Gln Ser Pro Ser Phe Leu Ser Ala Ser Val Gly
1               5                   10                  15

Asp Arg Val Thr Ile Thr Cys Arg Ala Ser His Gly Ile Asn Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys
            100

<210> SEQ ID NO 19
<211> LENGTH: 103
<212> TYPE: PRT
<213> ORGANISM: Artificial Sequence
<220> FEATURE:
<223> OTHER INFORMATION: synthetic protein

<400> SEQUENCE: 19

Glu Ile Val Leu Thr Gln Ser Pro Ser Thr Leu Ser Ala Ser Val Gly
1               5                   10                  15

Glu Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Val Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Leu Trp
                85                  90                  95

Thr Phe Gly Gln Gly Thr Lys
            100

<210> SEQ ID NO 20
<211> LENGTH: 103
<212> TYPE: PRT
<213> ORGANISM: Artificial Sequence
<220> FEATURE:
<223> OTHER INFORMATION: synthetic protein

<400> SEQUENCE: 20

Glu Ile Val Leu Thr Gln Ser Pro Ser Ile Leu Ser Ala Ser Val Gly
1               5                   10                  15

Asp Arg Val Thr Ile Thr Cys Arg Ala Ser His Gly Ile Asn Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys
            100

<210> SEQ ID NO 21
<211> LENGTH: 109
<212> TYPE: PRT
<213> ORGANISM: Artificial Sequence
<220> FEATURE:
<223> OTHER INFORMATION: synthetic protein
```

```
<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Asn Lys Asp Tyr Leu Ala Trp Tyr Gln Gln Lys Pro Gly Gln
        35                  40                  45

Ser Pro Arg Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Arg Leu Gln Ala Glu Asp Val Ala Val Tyr Tyr Cys Gln His
                85                  90                  95

Tyr Tyr Ser Tyr Pro Leu Thr Phe Gly Gln Gly Thr Lys
            100                 105

<210> SEQ ID NO 22
<211> LENGTH: 103
<212> TYPE: PRT
<213> ORGANISM: Artificial Sequence
<220> FEATURE:
<223> OTHER INFORMATION: synthetic protein

<400> SEQUENCE: 22

Glu Ile Val Leu Thr Gln Ser Pro Ser Thr Leu Ser Ala Ser Ile Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Gly Leu Leu Pro
65                  70                  75                  80

Glu Asp Phe Ala Ser Tyr Phe Cys Gln Gln Ala Ser Val Phe Pro Val
                85                  90                  95

Thr Phe Gly Gly Gly Thr Lys
            100

<210> SEQ ID NO 23
<211> LENGTH: 105
<212> TYPE: PRT
<213> ORGANISM: Artificial Sequence
<220> FEATURE:
<223> OTHER INFORMATION: synthetic protein

<400> SEQUENCE: 23

Glu Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Leu Gln Asp Ser Asn Pro Tyr Pro
                85                  90                  95

Leu Leu Thr Phe Gly Gly Gly Thr Lys
            100                 105

<210> SEQ ID NO 24
<211> LENGTH: 102
<212> TYPE: PRT
<213> ORGANISM: Artificial Sequence
<220> FEATURE:
<223> OTHER INFORMATION: synthetic protein

<400> SEQUENCE: 24

Glu Ile Val Leu Thr Gln Ser Pro Ser Phe Leu Ser Ala Ser Val Gly
1               5                   10                  15

Asp Arg Val Thr Ile Thr Cys Arg Ala Ser His Gly Ile Asn Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Ala Arg Thr Lys
            100

<210> SEQ ID NO 25
<211> LENGTH: 109
<212> TYPE: PRT
<213> ORGANISM: Artificial Sequence
<220> FEATURE:
<223> OTHER INFORMATION: synthetic protein

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Asn Lys Asp Tyr Leu Ala Trp Tyr Gln Gln Lys Pro Gly Gln
        35                  40                  45

Ser Pro Arg Leu Leu Ile Ser Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Asn Arg Leu Gln Ala Glu Asp Val Ala Val Tyr Tyr Cys Gln His
                85                  90                  95

Tyr Tyr Ser Tyr Pro Leu Thr Phe Gly Gln Gly Thr Lys
            100                 105

<210> SEQ ID NO 26
<211> LENGTH: 103
<212> TYPE: PRT
<213> ORGANISM: Artificial Sequence
<220> FEATURE:
<223> OTHER INFORMATION: synthetic protein

<400> SEQUENCE: 26

Asp Val Val Met Thr Gln Ser Pro Ser Thr Leu Ser Ala Ser Val Gly
1               5                   10                  15

Asp Arg Val Thr Ile Thr Cys Arg Ala Ser Glu Asn Ile Asn Arg Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Cys Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys His Gln Tyr Thr Thr Tyr Leu Trp
            85                  90                  95

Thr Phe Gly Gln Gly Thr Lys
            100

<210> SEQ ID NO 27
<211> LENGTH: 109
<212> TYPE: PRT
<213> ORGANISM: Artificial Sequence
<220> FEATURE:
<223> OTHER INFORMATION: synthetic protein

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Asn Lys Asp Tyr Leu Ala Trp Tyr Gln Gln Lys Pro Gly Gln
        35                  40                  45

Ser Pro Arg Leu Leu Ile Pro Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Asn Arg Leu Gln Ala Glu Asp Val Ala Val Tyr Tyr Cys Gln His
            85                  90                  95

Tyr Tyr Ser Tyr Pro Leu Thr Phe Gly Gln Gly Thr Lys
            100                 105

<210> SEQ ID NO 28
<211> LENGTH: 102
<212> TYPE: PRT
<213> ORGANISM: Artificial Sequence
<220> FEATURE:
<223> OTHER INFORMATION: synthetic protein

<400> SEQUENCE: 28

Glu Ile Val Leu Thr Gln Ser Pro Ser Thr Leu Ser Ala Ser Ile Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Gly Leu Leu Pro
65                  70                  75                  80

Glu Asp Phe Ala Ser Tyr Phe Cys Gln Gln Ala Ser Val Phe Pro Val
            85                  90                  95

Thr Phe Ala Arg Thr Lys
            100

<210> SEQ ID NO 29
<211> LENGTH: 103
<212> TYPE: PRT
<213> ORGANISM: Artificial Sequence
<220> FEATURE:
<223> OTHER INFORMATION: synthetic protein

<400> SEQUENCE: 29

Glu Ile Cys Val Thr Gln Ser Pro Ser Phe Leu Ser Ala Ser Val Gly
1               5                   10                  15

Asp Arg Val Thr Ile Thr Cys Arg Ala Ser His Gly Ile Asn Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys
            100

<210> SEQ ID NO 30
<211> LENGTH: 103
<212> TYPE: PRT
<213> ORGANISM: Artificial Sequence
<220> FEATURE:
<223> OTHER INFORMATION: synthetic protein

<400> SEQUENCE: 30

Glu Ile Val Leu Thr Gln Ser Pro Ser Thr Leu Ser Ala Ser Val Gly
1               5                   10                  15

Glu Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Leu Trp
                85                  90                  95

Thr Phe Gly Gln Gly Thr Lys
            100

<210> SEQ ID NO 31
<211> LENGTH: 103
<212> TYPE: PRT
<213> ORGANISM: Artificial Sequence
<220> FEATURE:
<223> OTHER INFORMATION: synthetic protein

<400> SEQUENCE: 31

Glu Ile Val Leu Thr Gln Ser Pro Ser Thr Leu Ser Ala Ser Val Gly
1               5                   10                  15

Glu Arg Val Thr Ile Thr Cys Arg Ala Ser Gln Ser Ile Ser Ser Trp
          20                  25                  30

Leu Ala Trp Tyr Gln Gln Lys Pro Gly Lys Ala Pro Lys Val Leu Ile
         35                  40                  45

Tyr Lys Ala Ser Ser Leu Glu Ser Gly Val Pro Asp Arg Phe Ser Gly
     50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Leu Trp
                 85                  90                  95

Thr Phe Gly Gln Gly Thr Lys
            100

<210> SEQ ID NO 32
<211> LENGTH: 109
<212> TYPE: PRT
<213> ORGANISM: Artificial Sequence
<220> FEATURE:
<223> OTHER INFORMATION: synthetic protein

<400> SEQUENCE: 32

Asp Ile Val Met Thr Lys Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Lys Asn Lys Asp Tyr Leu Ala Trp Tyr Gln Lys Lys Pro Gly Gln
        35                  40                  45

Ser Pro Arg Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Arg Leu Gln Ala Glu Asp Val Ala Val Tyr Tyr Cys Gln His
                85                  90                  95

Tyr Tyr Ser Tyr Pro Leu Thr Phe Gly Gln Gly Thr Lys
            100                 105

<210> SEQ ID NO 33
<211> LENGTH: 103
<212> TYPE: PRT
<213> ORGANISM: Artificial Sequence
<220> FEATURE:
<223> OTHER INFORMATION: synthetic protein

<400> SEQUENCE: 33

Glu Ile Val Leu Thr Gln Ser Pro Ser Thr Leu Ser Ala Ser Val Gly
1               5                   10                  15

Glu Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
         35                  40                  45

Tyr Lys Ala Ser Ser Leu Glu Ser Gly Val Pro Ser Phe Arg Ser Gly
     50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Leu Trp
                 85                  90                  95

Thr Phe Gly Gln Gly Thr Lys
            100

<210> SEQ ID NO 34
<211> LENGTH: 103
<212> TYPE: PRT
<213> ORGANISM: Artificial Sequence
<220> FEATURE:
<223> OTHER INFORMATION: synthetic protein

<400> SEQUENCE: 34

```
Glu Ile Val Leu Thr Gln Ser Pro Ser Thr Leu Ser Ala Ser Ile Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Gly Leu Leu Pro
65                  70                  75                  80

Glu Asp Phe Ala Ser Tyr Phe Cys Leu Gln Ala Ser Val Phe Pro Val
                85                  90                  95

Thr Phe Gly Gly Gly Thr Lys
            100
```

<210> SEQ ID NO 35
<211> LENGTH: 15
<212> TYPE: PRT
<213> ORGANISM: Artificial Sequence
<220> FEATURE:
<223> OTHER INFORMATION: synthetic protein

<400> SEQUENCE: 35

```
Gly Gly Gly Gly Ser Gly Gly Gly Gly Ser Gly Gly Gly Gly Ser
1               5                   10                  15
```

<210> SEQ ID NO 36
<211> LENGTH: 39
<212> TYPE: PRT
<213> ORGANISM: Artificial Sequence
<220> FEATURE:
<223> OTHER INFORMATION: synthetic protein

<400> SEQUENCE: 36

```
Ser His Gly Phe Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn
        35
```

<210> SEQ ID NO 37
<211> LENGTH: 9
<212> TYPE: PRT
<213> ORGANISM: Artificial Sequence
<220> FEATURE:
<223> OTHER INFORMATION: synthetic protein

<400> SEQUENCE: 37

```
Tyr Pro Tyr Asp Val Pro Asp Tyr Ala
1               5
```

<210> SEQ ID NO 38

```
<211> LENGTH: 40
<212> TYPE: PRT
<213> ORGANISM: Homo sapiens

<400> SEQUENCE: 38

Asn Pro Asp Phe Pro Pro Glu Val Glu Glu Gln Asp Ala Ser Thr Leu
1               5                   10                  15

Pro Val Ser Cys Ala Trp Glu Ser Gly Met Lys Arg His Arg Ala Ala
            20                  25                  30

Cys Ala Ser Ala Ser Ile Asn Val
        35                  40

<210> SEQ ID NO 39
<211> LENGTH: 40
<212> TYPE: PRT
<213> ORGANISM: Artificial Sequence
<220> FEATURE:
<223> OTHER INFORMATION: synthetic protein

<400> SEQUENCE: 39

Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 40
<211> LENGTH: 284
<212> TYPE: PRT
<213> ORGANISM: Artificial Sequence
<220> FEATURE:
<223> OTHER INFORMATION: synthetic protein

<400> SEQUENCE: 40

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Phe Leu Ser
    130                 135                 140

Ala Ser Val Gly Asp Arg Val Thr Ile Thr Cys Arg Ala Ser His Gly
145                 150                 155                 160

Ile Asn Asn Tyr Leu Ala Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190
```

```
Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Ala Asn
    210                 215                 220

Ser Phe Pro Leu Thr Phe Gly Gly Gly Thr Lys Tyr Pro Tyr Asp Val
225                 230                 235                 240

Pro Asp Tyr Ala Ser His Gly Phe Pro Pro Glu Val Glu Gln Asp
                245                 250                 255

Asp Gly Thr Leu Pro Met Ser Cys Ala Gln Glu Ser Gly Met Asp Arg
                260                 265                 270

His Pro Ala Ala Cys Ala Ser Ala Arg Ile Asn Val
            275                 280

<210> SEQ ID NO 41
<211> LENGTH: 284
<212> TYPE: PRT
<213> ORGANISM: Artificial Sequence
<220> FEATURE:
<223> OTHER INFORMATION: synthetic protein

<400> SEQUENCE: 41

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Thr Leu Ser
    130                 135                 140

Ala Ser Val Gly Glu Arg Val Thr Ile Thr Cys Arg Ala Ser Gln Ser
145                 150                 155                 160

Ile Ser Ser Trp Leu Ala Trp Tyr Gln Gln Lys Pro Gly Lys Ala Pro
                165                 170                 175

Lys Val Leu Ile Tyr Lys Ala Ser Ser Leu Glu Ser Gly Val Pro Ser
            180                 185                 190

Arg Phe Ser Gly Ser Gly Ser Gly Thr Glu Phe Thr Leu Thr Ile Ser
        195                 200                 205

Ser Leu Gln Pro Asp Asp Phe Ala Thr Tyr Tyr Cys Gln Gln Tyr Ser
    210                 215                 220

Thr Tyr Leu Trp Thr Phe Gly Gln Gly Thr Lys Tyr Pro Tyr Asp Val
225                 230                 235                 240

Pro Asp Tyr Ala Ser His Gly Phe Pro Pro Glu Val Glu Gln Asp
                245                 250                 255

Asp Gly Thr Leu Pro Met Ser Cys Ala Gln Glu Ser Gly Met Asp Arg
                260                 265                 270
```

His Pro Ala Ala Cys Ala Ser Ala Arg Ile Asn Val
        275                 280

<210> SEQ ID NO 42
<211> LENGTH: 284
<212> TYPE: PRT
<213> ORGANISM: Artificial Sequence
<220> FEATURE:
<223> OTHER INFORMATION: synthetic protein

<400> SEQUENCE: 42

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Ile Leu Ser
    130                 135                 140

Ala Ser Val Gly Asp Arg Val Thr Ile Thr Cys Arg Ala Ser His Gly
145                 150                 155                 160

Ile Asn Asn Tyr Leu Ala Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Asn
    210                 215                 220

Ser Phe Pro Trp Thr Phe Gly Gln Gly Thr Lys Tyr Pro Tyr Asp Val
225                 230                 235                 240

Pro Asp Tyr Ala Ser His Gly Phe Pro Pro Glu Val Glu Glu Gln Asp
                245                 250                 255

Asp Gly Thr Leu Pro Met Ser Cys Ala Gln Glu Ser Gly Met Asp Arg
            260                 265                 270

His Pro Ala Ala Cys Ala Ser Ala Arg Ile Asn Val
        275                 280

<210> SEQ ID NO 43
<211> LENGTH: 296
<212> TYPE: PRT
<213> ORGANISM: Artificial Sequence
<220> FEATURE:
<223> OTHER INFORMATION: synthetic protein

<400> SEQUENCE: 43

Gln Val Gln Leu Val Glu Ser Gly Gly Gly Leu Val Lys Pro Gly Gly

```
1               5                   10                  15
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Ala Val Gly Asn Pro Gln Gly Tyr Phe Asp Phe
            100                 105                 110

Trp Gly Arg Gly Thr Leu Val Thr Val Ser Ser Gly Gly Gly Gly Ser
            115                 120                 125

Gly Gly Gly Gly Ser Gly Gly Gly Ser Asp Ile Val Met Thr Gln
        130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Asn Lys Asp Tyr
                165                 170                 175

Leu Ala Trp Tyr Gln Gln Lys Pro Gly Gln Ser Pro Arg Leu Leu Ile
            180                 185                 190

Ser Trp Ala Ser Thr Arg Glu Ser Gly Val Pro Asp Arg Phe Ser Gly
            195                 200                 205

Ser Gly Ser Gly Thr Asp Phe Thr Leu Thr Ile Asn Arg Leu Gln Ala
    210                 215                 220

Glu Asp Val Ala Val Tyr Tyr Cys Gln His Tyr Tyr Ser Tyr Pro Leu
225                 230                 235                 240

Thr Phe Gly Gln Gly Thr Lys Tyr Pro Tyr Asp Val Pro Asp Tyr Ala
                245                 250                 255

Ser His Gly Phe Pro Pro Glu Val Glu Glu Gln Asp Asp Gly Thr Leu
            260                 265                 270

Pro Met Ser Cys Ala Gln Glu Ser Gly Met Asp Arg His Pro Ala Ala
            275                 280                 285

Cys Ala Ser Ala Arg Ile Asn Val
        290                 295

<210> SEQ ID NO 44
<211> LENGTH: 284
<212> TYPE: PRT
<213> ORGANISM: Artificial Sequence
<220> FEATURE:
<223> OTHER INFORMATION: synthetic protein

<400> SEQUENCE: 44

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ser Met Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
```

-continued

```
                65                  70                  75                  80
Leu Gln Met Asn Ser Leu Arg Ala Glu Asp Thr Ala Val Tyr Tyr Cys
                    85                  90                  95

Ala Arg Asp Leu Arg Gly Ala Leu Asp Tyr Trp Gly Gln Gly Thr Leu
                100                 105                 110

Val Thr Val Ser Ser Gly Gly Gly Gly Ser Gly Gly Gly Gly Ser Gly
                115                 120                 125

Gly Gly Gly Ser Glu Ile Val Leu Thr Gln Ser Pro Ser Thr Leu Ser
        130                 135                 140

Ala Ser Ile Gly Asp Arg Val Thr Ile Thr Cys Arg Ala Ser Gln Gly
145                 150                 155                 160

Ile Ser Asn Tyr Leu Ala Trp Tyr Gln Gln Lys Pro Gly Lys Ala Pro
                165                 170                 175

Lys Leu Leu Ile Tyr Ala Ala Ser Thr Leu Gln Ser Gly Val Pro Ser
                180                 185                 190

Arg Phe Ser Gly Ser Gly Ser Gly Thr Glu Phe Thr Leu Thr Ile Ser
            195                 200                 205

Gly Leu Leu Pro Glu Asp Phe Ala Ser Tyr Phe Cys Gln Gln Ala Ser
        210                 215                 220

Val Phe Pro Val Thr Phe Gly Gly Gly Thr Lys Tyr Pro Tyr Asp Val
225                 230                 235                 240

Pro Asp Tyr Ala Ser His Gly Phe Pro Pro Glu Val Glu Glu Gln Asp
                245                 250                 255

Asp Gly Thr Leu Pro Met Ser Cys Ala Gln Glu Ser Gly Met Asp Arg
            260                 265                 270

His Pro Ala Ala Cys Ala Ser Ala Arg Ile Asn Val
                275                 280
```

<210> SEQ ID NO 45
<211> LENGTH: 292
<212> TYPE: PRT
<213> ORGANISM: Artificial Sequence
<220> FEATURE:
<223> OTHER INFORMATION: synthetic protein

<400> SEQUENCE: 45

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Asp Gly Ile Ala Ala Arg Ser Gly Tyr Tyr Gly Met Asp Val
                100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Glu Ile Val Leu Thr Gln
        130                 135                 140

Ser Pro Ser Thr Leu Ser Ala Ser Val Gly Asp Arg Val Thr Ile Thr
```

```
              145                 150                 155                 160
Cys Arg Ala Ser Gln Ser Ile Ser Ser Trp Leu Ala Trp Tyr Gln Gln
                    165                 170                 175

Lys Pro Gly Lys Ala Pro Lys Leu Leu Ile Tyr Ala Ala Ser Ile Leu
                180                 185                 190

Gln Ser Gly Val Pro Ser Arg Phe Ser Gly Ser Gly Ser Gly Thr Asp
            195                 200                 205

Phe Thr Leu Thr Ile Ser Ser Leu Gln Pro Glu Asp Phe Ala Thr Tyr
        210                 215                 220

Tyr Cys Leu Gln Asp Ser Asn Pro Tyr Pro Leu Leu Thr Phe Gly Gly
225                 230                 235                 240

Gly Thr Lys Tyr Pro Tyr Asp Val Pro Asp Tyr Ala Ser His Gly Phe
                245                 250                 255

Pro Pro Glu Val Glu Glu Gln Asp Asp Gly Thr Leu Pro Met Ser Cys
                260                 265                 270

Ala Gln Glu Ser Gly Met Asp Arg His Pro Ala Ala Cys Ala Ser Ala
                275                 280                 285

Arg Ile Asn Val
            290

<210> SEQ ID NO 46
<211> LENGTH: 283
<212> TYPE: PRT
<213> ORGANISM: Artificial Sequence
<220> FEATURE:
<223> OTHER INFORMATION: synthetic protein

<400> SEQUENCE: 46

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Phe Leu Ser
    130                 135                 140

Ala Ser Val Gly Asp Arg Val Thr Ile Thr Cys Arg Ala Ser His Gly
145                 150                 155                 160

Ile Asn Asn Tyr Leu Ala Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Asn
```

```
                210                 215                 220
Ser Phe Pro Leu Thr Phe Ala Arg Thr Lys Tyr Pro Tyr Asp Val Pro
225                 230                 235                 240

Asp Tyr Ala Ser His Gly Phe Pro Pro Glu Val Glu Glu Gln Asp Asp
                245                 250                 255

Gly Thr Leu Pro Met Ser Cys Ala Gln Glu Ser Gly Met Asp Arg His
                260                 265                 270

Pro Ala Ala Cys Ala Ser Ala Arg Ile Asn Val
                275                 280

<210> SEQ ID NO 47
<211> LENGTH: 296
<212> TYPE: PRT
<213> ORGANISM: Artificial Sequence
<220> FEATURE:
<223> OTHER INFORMATION: synthetic protein

<400> SEQUENCE: 47

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
        50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Ala Val Gly Asn Pro Gln Gly Tyr Phe Asp Phe
                100                 105                 110

Trp Gly Arg Gly Thr Leu Val Thr Val Ser Ser Gly Gly Gly Gly Ser
            115                 120                 125

Gly Gly Gly Gly Ser Gly Gly Gly Ser Asp Ile Val Met Thr Gln
130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Asn Lys Asp Tyr
                165                 170                 175

Leu Ala Trp Tyr Gln Gln Lys Pro Gly Gln Ser Pro Arg Leu Leu Ile
            180                 185                 190

Ser Trp Ala Ser Thr Arg Glu Ser Gly Val Pro Ser Arg Phe Ser Gly
            195                 200                 205

Ser Gly Ser Gly Thr Asp Phe Thr Leu Thr Ile Asn Arg Leu Gln Ala
        210                 215                 220

Glu Asp Val Ala Val Tyr Tyr Cys Gln His Tyr Tyr Ser Tyr Pro Leu
225                 230                 235                 240

Thr Phe Gly Gln Gly Thr Lys Tyr Pro Tyr Asp Val Pro Asp Tyr Ala
                245                 250                 255

Ser His Gly Phe Pro Pro Glu Val Glu Glu Gln Asp Asp Gly Thr Leu
                260                 265                 270

Pro Met Ser Cys Ala Gln Glu Ser Gly Met Asp Arg His Pro Ala Ala
                275                 280                 285

Cys Ala Ser Ala Arg Ile Asn Val
```

<210> SEQ ID NO 48
<211> LENGTH: 284
<212> TYPE: PRT
<213> ORGANISM: Artificial Sequence
<220> FEATURE:
<223> OTHER INFORMATION: synthetic protein

<400> SEQUENCE: 48

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Pro Asp Ser Asn Gly Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Asp Val Val Met Thr Gln Ser Pro Ser Thr Leu Ser
    130                 135                 140

Ala Ser Val Gly Asp Arg Val Thr Ile Thr Cys Arg Ala Ser Glu Asn
145                 150                 155                 160

Ile Asn Arg Trp Leu Ala Trp Tyr Gln Gln Lys Pro Gly Lys Ala Pro
                165                 170                 175

Lys Leu Leu Ile Tyr Lys Ala Ser Ser Leu Glu Ser Gly Val Pro Ser
            180                 185                 190

Arg Cys Ser Gly Ser Gly Ser Gly Thr Glu Phe Thr Leu Thr Ile Ser
        195                 200                 205

Ser Leu Gln Pro Asp Asp Phe Ala Thr Tyr Tyr Cys His Gln Tyr Thr
    210                 215                 220

Thr Tyr Leu Trp Thr Phe Gly Gln Gly Thr Lys Tyr Pro Tyr Asp Val
225                 230                 235                 240

Pro Asp Tyr Ala Ser His Gly Phe Pro Pro Glu Val Glu Glu Gln Asp
                245                 250                 255

Asp Gly Thr Leu Pro Met Ser Cys Ala Gln Glu Ser Gly Met Asp Arg
            260                 265                 270

His Pro Ala Ala Cys Ala Ser Ala Arg Ile Asn Val
        275                 280
```

<210> SEQ ID NO 49
<211> LENGTH: 296
<212> TYPE: PRT
<213> ORGANISM: Artificial Sequence
<220> FEATURE:
<223> OTHER INFORMATION: synthetic protein

<400> SEQUENCE: 49

```
Gln Val Gln Leu Val Glu Ser Gly Gly Gly Leu Val Lys Pro Gly Gly
1               5                   10                  15
```

-continued

```
Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ala Ala Ile Ser Gly Ser Gly Asp Asn Thr Tyr Tyr Ala Asp Ser Val
     50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                 85                  90                  95

Ala Lys Asp Gly Pro Ala Val Gly Asn Pro Gly Gly Tyr Phe Asp Phe
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Ser Asp Ile Val Met Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Asn Lys Asp Tyr
                165                 170                 175

Leu Ala Trp Tyr Gln Gln Lys Pro Gly Gln Ser Pro Arg Leu Leu Ile
            180                 185                 190

Pro Trp Ala Ser Thr Arg Glu Ser Gly Val Pro Asp Arg Phe Ser Gly
        195                 200                 205

Ser Gly Ser Gly Thr Asp Phe Thr Leu Thr Ile Asn Arg Leu Gln Ala
    210                 215                 220

Glu Asp Val Ala Val Tyr Tyr Cys Gln His Tyr Tyr Ser Tyr Pro Leu
225                 230                 235                 240

Thr Phe Gly Gln Gly Thr Lys Tyr Pro Tyr Asp Val Pro Asp Tyr Ala
                245                 250                 255

Ser His Gly Phe Pro Pro Glu Val Glu Glu Asp Asp Gly Thr Leu
            260                 265                 270

Pro Met Ser Cys Ala Gln Glu Ser Gly Met Asp Arg His Pro Ala Ala
        275                 280                 285

Cys Ala Ser Ala Arg Ile Asn Val
    290                 295

<210> SEQ ID NO 50
<211> LENGTH: 283
<212> TYPE: PRT
<213> ORGANISM: Artificial Sequence
<220> FEATURE:
<223> OTHER INFORMATION: synthetic protein

<400> SEQUENCE: 50

Gln Val Gln Leu Val Gln Ser Gly Gly Gly Val Val His Pro Gly Arg
1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ser Met Ser Tyr Asp Gly Asn Asn Lys Tyr Tyr Ala Asp Ser Val
     50                  55                  60

Lys Gly Arg Phe Thr Thr Pro Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Asp Leu Arg Gly Ala Leu Asp Tyr Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Glu Ile Val Leu Thr Gln Ser Pro Ser Thr Leu Ser
        130                 135                 140

Ala Ser Ile Gly Asp Arg Val Thr Ile Thr Cys Arg Ala Ser Gln Gly
145                 150                 155                 160

Ile Ser Asn Tyr Leu Ala Trp Tyr Gln Gln Lys Pro Gly Lys Ala Pro
                165                 170                 175

Lys Leu Leu Ile Tyr Ala Ala Ser Thr Leu Gln Ser Gly Val Pro Ser
            180                 185                 190

Arg Phe Ser Gly Ser Gly Ser Gly Thr Glu Phe Thr Leu Thr Ile Ser
        195                 200                 205

Gly Leu Leu Pro Glu Asp Phe Ala Ser Tyr Phe Cys Gln Gln Ala Ser
        210                 215                 220

Val Phe Pro Val Thr Phe Ala Arg Thr Lys Tyr Pro Tyr Asp Val Pro
225                 230                 235                 240

Asp Tyr Ala Ser His Gly Phe Pro Pro Glu Val Glu Glu Gln Asp Asp
                245                 250                 255

Gly Thr Leu Pro Met Ser Cys Ala Gln Glu Ser Gly Met Asp Arg His
            260                 265                 270

Pro Ala Ala Cys Ala Ser Ala Arg Ile Asn Val
        275                 280

<210> SEQ ID NO 51
<211> LENGTH: 284
<212> TYPE: PRT
<213> ORGANISM: Artificial Sequence
<220> FEATURE:
<223> OTHER INFORMATION: synthetic protein

<400> SEQUENCE: 51

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Cys Val Thr Gln Ser Pro Ser Phe Leu Ser
        130                 135                 140

Ala Ser Val Gly Asp Arg Val Thr Ile Thr Cys Arg Ala Ser His Gly
145                 150                 155                 160
```

```
Ile Asn Asn Tyr Leu Ala Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Asn
    210                 215                 220

Ser Phe Pro Leu Thr Phe Gly Gly Gly Thr Lys Tyr Pro Tyr Asp Val
225                 230                 235                 240

Pro Asp Tyr Ala Ser His Gly Phe Pro Pro Glu Val Glu Gln Asp
                245                 250                 255

Asp Gly Thr Leu Pro Met Ser Cys Ala Gln Glu Ser Gly Met Asp Arg
            260                 265                 270

His Pro Ala Ala Cys Ala Ser Ala Arg Ile Asn Val
                275                 280
```

<210> SEQ ID NO 52
<211> LENGTH: 284
<212> TYPE: PRT
<213> ORGANISM: Artificial Sequence
<220> FEATURE:
<223> OTHER INFORMATION: synthetic protein

<400> SEQUENCE: 52

```
Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Ala Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Ala Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Thr Leu Ser
    130                 135                 140

Ala Ser Val Gly Glu Arg Val Thr Ile Thr Cys Arg Ala Ser Gln Ser
145                 150                 155                 160

Ile Ser Ser Trp Leu Ala Trp Tyr Gln Gln Lys Pro Gly Lys Ala Pro
                165                 170                 175

Lys Val Leu Ile Tyr Lys Ala Ser Ser Leu Glu Ser Gly Val Pro Ser
            180                 185                 190

Arg Phe Ser Gly Ser Gly Ser Gly Thr Glu Phe Thr Leu Thr Ile Ser
        195                 200                 205

Ser Leu Gln Pro Asp Asp Phe Ala Thr Tyr Tyr Cys Gln Gln Tyr Ser
    210                 215                 220

Thr Tyr Leu Trp Thr Phe Gly Gln Gly Thr Lys Tyr Pro Tyr Asp Val
225                 230                 235                 240
```

```
Pro Asp Tyr Ala Ser His Gly Phe Pro Pro Glu Val Glu Glu Gln Asp
            245                 250                 255

Asp Gly Thr Leu Pro Met Ser Cys Ala Gln Glu Ser Gly Met Asp Arg
        260                 265                 270

His Pro Ala Ala Cys Ala Ser Ala Arg Ile Asn Val
    275                 280

<210> SEQ ID NO 53
<211> LENGTH: 284
<212> TYPE: PRT
<213> ORGANISM: Artificial Sequence
<220> FEATURE:
<223> OTHER INFORMATION: synthetic protein

<400> SEQUENCE: 53

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Leu Val Gly Ala Lys Gly Asn Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Thr Leu Ser
    130                 135                 140

Ala Ser Val Gly Glu Arg Val Thr Ile Thr Cys Arg Ala Ser Gln Ser
145                 150                 155                 160

Ile Ser Ser Trp Leu Ala Trp Tyr Gln Gln Lys Pro Gly Lys Ala Pro
                165                 170                 175

Lys Val Leu Ile Tyr Lys Ala Ser Ser Leu Glu Ser Gly Val Pro Asp
            180                 185                 190

Arg Phe Ser Gly Ser Gly Ser Gly Thr Glu Phe Thr Leu Thr Ile Ser
        195                 200                 205

Ser Leu Gln Pro Asp Asp Phe Ala Thr Tyr Tyr Cys Gln Gln Tyr Ser
    210                 215                 220

Thr Tyr Leu Trp Thr Phe Gly Gln Gly Thr Lys Tyr Pro Tyr Asp Val
225                 230                 235                 240

Pro Asp Tyr Ala Ser His Gly Phe Pro Pro Glu Val Glu Glu Gln Asp
            245                 250                 255

Asp Gly Thr Leu Pro Met Ser Cys Ala Gln Glu Ser Gly Met Asp Arg
        260                 265                 270

His Pro Ala Ala Cys Ala Ser Ala Arg Ile Asn Val
    275                 280

<210> SEQ ID NO 54
<211> LENGTH: 296
<212> TYPE: PRT
<213> ORGANISM: Artificial Sequence
<220> FEATURE:
```

<223> OTHER INFORMATION: synthetic protein

<400> SEQUENCE: 54

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Glu Val Gly Asn Pro Gly Gly Tyr Phe Asp Phe
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Ser Asp Ile Val Met Thr Lys
    130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Lys Asn Lys Asp Tyr
                165                 170                 175

Leu Ala Trp Tyr Gln Lys Lys Pro Gly Gln Ser Pro Arg Leu Leu Ile
            180                 185                 190

Ser Trp Ala Ser Thr Arg Glu Ser Gly Val Pro Asp Arg Phe Ser Gly
        195                 200                 205

Ser Gly Ser Gly Thr Asp Phe Thr Leu Thr Ile Asn Arg Leu Gln Ala
    210                 215                 220

Glu Asp Val Ala Val Tyr Tyr Cys Gln His Tyr Tyr Ser Tyr Pro Leu
225                 230                 235                 240

Thr Phe Gly Gln Gly Thr Lys Tyr Pro Tyr Asp Val Pro Asp Tyr Ala
                245                 250                 255

Ser His Gly Phe Pro Pro Glu Val Glu Glu Gln Asp Asp Gly Thr Leu
            260                 265                 270

Pro Met Ser Cys Ala Gln Glu Ser Gly Met Asp Arg His Pro Ala Ala
        275                 280                 285

Cys Ala Ser Ala Arg Ile Asn Val
    290                 295
```

<210> SEQ ID NO 55
<211> LENGTH: 284
<212> TYPE: PRT
<213> ORGANISM: Artificial Sequence
<220> FEATURE:
<223> OTHER INFORMATION: synthetic protein

<400> SEQUENCE: 55

```
Gln Val Gln Leu Gln Gln Ser Gly Glu Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

```
Ala Val Ile Ser Tyr Asp Gly Ser Asn Lys Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Val Gly Ala Lys Gly Asn Trp Gly Gln Gly Thr Leu
                100                 105                 110

Val Thr Val Ser Ser Gly Gly Gly Gly Ser Gly Gly Gly Gly Ser Gly
                115                 120                 125

Gly Gly Gly Ser Glu Ile Val Leu Thr Gln Ser Pro Ser Thr Leu Ser
        130                 135                 140

Ala Ser Val Gly Glu Arg Val Thr Ile Thr Cys Arg Ala Ser Gln Ser
145                 150                 155                 160

Ile Ser Ser Trp Leu Ala Trp Tyr Gln Gln Lys Pro Gly Lys Ala Pro
                165                 170                 175

Lys Val Leu Ile Tyr Lys Ala Ser Ser Leu Glu Ser Gly Val Pro Ser
                180                 185                 190

Phe Arg Ser Gly Ser Gly Ser Gly Thr Glu Phe Thr Leu Thr Ile Ser
                195                 200                 205

Ser Leu Gln Pro Asp Asp Phe Ala Thr Tyr Tyr Cys Gln Gln Tyr Ser
        210                 215                 220

Thr Tyr Leu Trp Thr Phe Gly Gln Gly Thr Lys Tyr Pro Tyr Asp Val
225                 230                 235                 240

Pro Asp Tyr Ala Ser His Gly Phe Pro Pro Glu Val Glu Glu Gln Asp
                245                 250                 255

Asp Gly Thr Leu Pro Met Ser Cys Ala Gln Glu Ser Gly Met Asp Arg
                260                 265                 270

His Pro Ala Ala Cys Ala Ser Ala Arg Ile Asn Val
                275                 280

<210> SEQ ID NO 56
<211> LENGTH: 284
<212> TYPE: PRT
<213> ORGANISM: Artificial Sequence
<220> FEATURE:
<223> OTHER INFORMATION: Synthetic protein

<400> SEQUENCE: 56

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
            35                  40                  45

Ala Ser Met Ser Tyr Asp Gly Asp Asn Lys Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Arg Gly Ala Leu Asp Tyr Trp Gly Gln Gly Thr Leu
                100                 105                 110

Val Thr Val Ser Ser Gly Gly Gly Gly Ser Gly Gly Gly Gly Ser Gly
                115                 120                 125
```

Gly Gly Gly Ser Glu Ile Val Leu Thr Gln Ser Pro Ser Thr Leu Ser
            130                 135                 140

Ala Ser Ile Gly Asp Arg Val Thr Ile Thr Cys Arg Ala Ser Gln Gly
145                 150                 155                 160

Ile Ser Asn Tyr Leu Ala Trp Tyr Gln Gln Lys Pro Gly Lys Ala Pro
                165                 170                 175

Lys Leu Leu Ile Tyr Ala Ala Ser Thr Leu Gln Ser Gly Val Pro Ser
                180                 185                 190

Arg Phe Ser Gly Ser Gly Ser Gly Thr Glu Phe Thr Leu Thr Ile Ser
            195                 200                 205

Gly Leu Leu Pro Glu Asp Phe Ala Ser Tyr Phe Cys Leu Gln Ala Ser
            210                 215                 220

Val Phe Pro Val Thr Phe Gly Gly Gly Thr Lys Tyr Pro Tyr Asp Val
225                 230                 235                 240

Pro Asp Tyr Ala Ser His Gly Phe Pro Pro Glu Val Glu Gln Asp
                245                 250                 255

Asp Gly Thr Leu Pro Met Ser Cys Ala Gln Glu Ser Gly Met Asp Arg
            260                 265                 270

His Pro Ala Ala Cys Ala Ser Ala Arg Ile Asn Val
            275                 280

<210> SEQ ID NO 57
<211> LENGTH: 284
<212> TYPE: PRT
<213> ORGANISM: Artificial Sequence
<220> FEATURE:
<223> OTHER INFORMATION: synthetic protein

<400> SEQUENCE: 57

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Glu Ile Val Leu Thr Gln Ser Pro Ser Phe Leu Ser
            130                 135                 140

Ala Ser Val Gly Asp Arg Val Thr Ile Thr Cys Arg Ala Ser His Gly
145                 150                 155                 160

Ile Asn Asn Tyr Leu Ala Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
                180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Ala Asn
210                 215                 220

Ser Phe Pro Leu Thr Phe Gly Gly Gly Thr Lys Tyr Pro Tyr Asp Val
225                 230                 235                 240

Pro Asp Tyr Ala Asn Pro Asp Phe Pro Pro Glu Val Glu Glu Gln Asp
            245                 250                 255

Ala Ser Thr Leu Pro Val Ser Cys Ala Trp Glu Ser Gly Met Lys Arg
            260                 265                 270

His Arg Ala Ala Cys Ala Ser Ala Ser Ile Asn Val
            275                 280

<210> SEQ ID NO 58
<211> LENGTH: 284
<212> TYPE: PRT
<213> ORGANISM: Artificial Sequence
<220> FEATURE:
<223> OTHER INFORMATION: synthetic protein

<400> SEQUENCE: 58

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Thr Leu Ser
130                 135                 140

Ala Ser Val Gly Glu Arg Val Thr Ile Thr Cys Arg Ala Ser Gln Ser
145                 150                 155                 160

Ile Ser Ser Trp Leu Ala Trp Tyr Gln Gln Lys Pro Gly Lys Ala Pro
                165                 170                 175

Lys Val Leu Ile Tyr Lys Ala Ser Ser Leu Glu Ser Gly Val Pro Ser
            180                 185                 190

Arg Phe Ser Gly Ser Gly Ser Gly Thr Glu Phe Thr Leu Thr Ile Ser
        195                 200                 205

Ser Leu Gln Pro Asp Asp Phe Ala Thr Tyr Tyr Cys Gln Gln Tyr Ser
210                 215                 220

Thr Tyr Leu Trp Thr Phe Gly Gln Gly Thr Lys Tyr Pro Tyr Asp Val
225                 230                 235                 240

Pro Asp Tyr Ala Asn Pro Asp Phe Pro Pro Glu Val Glu Glu Gln Asp
            245                 250                 255

Ala Ser Thr Leu Pro Val Ser Cys Ala Trp Glu Ser Gly Met Lys Arg
            260                 265                 270

His Arg Ala Ala Cys Ala Ser Ala Ser Ile Asn Val
            275                 280

```
<210> SEQ ID NO 59
<211> LENGTH: 284
<212> TYPE: PRT
<213> ORGANISM: Artificial Sequence
<220> FEATURE:
<223> OTHER INFORMATION: synthetic protein

<400> SEQUENCE: 59
```

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Glu Ile Val Leu Thr Gln Ser Pro Ser Ile Leu Ser
    130                 135                 140

Ala Ser Val Gly Asp Arg Val Thr Ile Thr Cys Arg Ala Ser His Gly
145                 150                 155                 160

Ile Asn Asn Tyr Leu Ala Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Asn
    210                 215                 220

Ser Phe Pro Trp Thr Phe Gly Gln Gly Thr Lys Tyr Pro Tyr Asp Val
225                 230                 235                 240

Pro Asp Tyr Ala Asn Pro Asp Phe Pro Pro Glu Val Glu Glu Gln Asp
                245                 250                 255

Ala Ser Thr Leu Pro Val Ser Cys Ala Trp Glu Ser Gly Met Lys Arg
            260                 265                 270

His Arg Ala Ala Cys Ala Ser Ala Ser Ile Asn Val
        275                 280

```
<210> SEQ ID NO 60
<211> LENGTH: 296
<212> TYPE: PRT
<213> ORGANISM: Artificial Sequence
<220> FEATURE:
<223> OTHER INFORMATION: synthetic protein

<400> SEQUENCE: 60
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr

```
                  20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Ala Val Gly Asn Pro Gln Gly Tyr Phe Asp Phe
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Gly Ser Asp Ile Val Met Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Asn Lys Asp Tyr
                165                 170                 175

Leu Ala Trp Tyr Gln Gln Lys Pro Gly Gln Ser Pro Arg Leu Leu Ile
            180                 185                 190

Ser Trp Ala Ser Thr Arg Glu Ser Gly Val Pro Asp Arg Phe Ser Gly
        195                 200                 205

Ser Gly Ser Gly Thr Asp Phe Thr Leu Thr Ile Asn Arg Leu Gln Ala
    210                 215                 220

Glu Asp Val Ala Val Tyr Tyr Cys Gln His Tyr Ser Tyr Pro Leu
225                 230                 235                 240

Thr Phe Gly Gln Gly Thr Lys Tyr Pro Tyr Asp Val Pro Asp Tyr Ala
            245                 250                 255

Asn Pro Asp Phe Pro Pro Glu Val Glu Glu Gln Asp Ala Ser Thr Leu
            260                 265                 270

Pro Val Ser Cys Ala Trp Glu Ser Gly Met Lys Arg His Arg Ala Ala
        275                 280                 285

Cys Ala Ser Ala Ser Ile Asn Val
    290                 295

<210> SEQ ID NO 61
<211> LENGTH: 284
<212> TYPE: PRT
<213> ORGANISM: Artificial Sequence
<220> FEATURE:
<223> OTHER INFORMATION: synthetic protein

<400> SEQUENCE: 61

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ser Met Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                       85                  90                  95
Ala Arg Asp Leu Arg Gly Ala Leu Asp Tyr Trp Gly Gln Gly Thr Leu
                100                 105                 110

Val Thr Val Ser Ser Gly Gly Gly Ser Gly Gly Gly Gly Ser Gly
            115                 120                 125

Gly Gly Gly Ser Glu Ile Val Leu Thr Gln Ser Pro Ser Thr Leu Ser
            130                 135                 140

Ala Ser Ile Gly Asp Arg Val Thr Ile Thr Cys Arg Ala Ser Gln Gly
145                 150                 155                 160

Ile Ser Asn Tyr Leu Ala Trp Tyr Gln Gln Lys Pro Gly Lys Ala Pro
                165                 170                 175

Lys Leu Leu Ile Tyr Ala Ala Ser Thr Leu Gln Ser Gly Val Pro Ser
                180                 185                 190

Arg Phe Ser Gly Ser Gly Ser Gly Thr Glu Phe Thr Leu Thr Ile Ser
                195                 200                 205

Gly Leu Leu Pro Glu Asp Phe Ala Ser Tyr Phe Cys Gln Gln Ala Ser
            210                 215                 220

Val Phe Pro Val Thr Phe Gly Gly Gly Thr Lys Tyr Pro Tyr Asp Val
225                 230                 235                 240

Pro Asp Tyr Ala Asn Pro Asp Phe Pro Pro Glu Val Glu Glu Gln Asp
                245                 250                 255

Ala Ser Thr Leu Pro Val Ser Cys Ala Trp Glu Ser Gly Met Lys Arg
                260                 265                 270

His Arg Ala Ala Cys Ala Ser Ala Ser Ile Asn Val
                275                 280

<210> SEQ ID NO 62
<211> LENGTH: 292
<212> TYPE: PRT
<213> ORGANISM: Artificial Sequence
<220> FEATURE:
<223> OTHER INFORMATION: synthetic protein

<400> SEQUENCE: 62

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Ala Ala Arg Ser Gly Tyr Tyr Gly Met Asp Val
                100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Glu Ile Val Leu Thr Gln
            130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Ser Trp Leu Ala Trp Tyr Gln Gln
```

```
                    165                 170                 175
Lys Pro Gly Lys Ala Pro Lys Leu Leu Ile Tyr Ala Ala Ser Ile Leu
                180                 185                 190

Gln Ser Gly Val Pro Ser Arg Phe Ser Gly Ser Gly Ser Gly Thr Asp
            195                 200                 205

Phe Thr Leu Thr Ile Ser Ser Leu Gln Pro Glu Asp Phe Ala Thr Tyr
        210                 215                 220

Tyr Cys Leu Gln Asp Ser Asn Pro Tyr Pro Leu Leu Thr Phe Gly Gly
225                 230                 235                 240

Gly Thr Lys Tyr Pro Tyr Asp Val Pro Asp Tyr Ala Asn Pro Asp Phe
                245                 250                 255

Pro Pro Glu Val Glu Glu Gln Asp Ala Ser Thr Leu Pro Val Ser Cys
            260                 265                 270

Ala Trp Glu Ser Gly Met Lys Arg His Arg Ala Ala Cys Ala Ser Ala
        275                 280                 285

Ser Ile Asn Val
    290

<210> SEQ ID NO 63
<211> LENGTH: 283
<212> TYPE: PRT
<213> ORGANISM: Artificial Sequence
<220> FEATURE:
<223> OTHER INFORMATION: synthetic protein

<400> SEQUENCE: 63

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Phe Leu Ser
    130                 135                 140

Ala Ser Val Gly Asp Arg Val Thr Ile Thr Cys Arg Ala Ser His Gly
145                 150                 155                 160

Ile Asn Asn Tyr Leu Ala Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Asn
    210                 215                 220

Ser Phe Pro Leu Thr Phe Ala Arg Thr Lys Tyr Pro Tyr Asp Val Pro
```

```
                225                 230                 235                 240
Asp Tyr Ala Asn Pro Asp Phe Pro Pro Glu Val Glu Glu Gln Asp Ala
                    245                 250                 255

Ser Thr Leu Pro Val Ser Cys Ala Trp Glu Ser Gly Met Lys Arg His
                260                 265                 270

Arg Ala Ala Cys Ala Ser Ala Ser Ile Asn Val
                275                 280

<210> SEQ ID NO 64
<211> LENGTH: 296
<212> TYPE: PRT
<213> ORGANISM: Artificial Sequence
<220> FEATURE:
<223> OTHER INFORMATION: synthetic protein

<400> SEQUENCE: 64

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Ala Val Gly Asn Pro Gln Gly Tyr Phe Asp Phe
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Ser Asp Ile Val Met Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Asn Lys Asp Tyr
                165                 170                 175

Leu Ala Trp Tyr Gln Gln Lys Pro Gly Gln Ser Pro Arg Leu Leu Ile
            180                 185                 190

Ser Trp Ala Ser Thr Arg Glu Ser Gly Val Pro Ser Arg Phe Ser Gly
        195                 200                 205

Ser Gly Ser Gly Thr Asp Phe Thr Leu Thr Ile Asn Arg Leu Gln Ala
    210                 215                 220

Glu Asp Val Ala Val Tyr Tyr Cys Gln His Tyr Tyr Ser Tyr Pro Leu
225                 230                 235                 240

Thr Phe Gly Gln Gly Thr Lys Tyr Pro Tyr Asp Val Pro Asp Tyr Ala
                245                 250                 255

Asn Pro Asp Phe Pro Pro Glu Val Glu Glu Gln Asp Ala Ser Thr Leu
            260                 265                 270

Pro Val Ser Cys Ala Trp Glu Ser Gly Met Lys Arg His Arg Ala Ala
        275                 280                 285

Cys Ala Ser Ala Ser Ile Asn Val
    290                 295
```

```
<210> SEQ ID NO 65
<211> LENGTH: 284
<212> TYPE: PRT
<213> ORGANISM: Artificial Sequence
<220> FEATURE:
<223> OTHER INFORMATION: synthetic protein

<400> SEQUENCE: 65
```

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Pro Asp Ser Asn Gly Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Asp Val Val Met Thr Gln Ser Pro Ser Thr Leu Ser
    130                 135                 140

Ala Ser Val Gly Asp Arg Val Thr Ile Thr Cys Arg Ala Ser Glu Asn
145                 150                 155                 160

Ile Asn Arg Trp Leu Ala Trp Tyr Gln Gln Lys Pro Gly Lys Ala Pro
                165                 170                 175

Lys Leu Leu Ile Tyr Lys Ala Ser Ser Leu Glu Ser Gly Val Pro Ser
            180                 185                 190

Arg Cys Ser Gly Ser Gly Ser Gly Thr Glu Phe Thr Leu Thr Ile Ser
        195                 200                 205

Ser Leu Gln Pro Asp Asp Phe Ala Thr Tyr Tyr Cys His Gln Tyr Thr
    210                 215                 220

Thr Tyr Leu Trp Thr Phe Gly Gln Gly Thr Lys Tyr Pro Tyr Asp Val
225                 230                 235                 240

Pro Asp Tyr Ala Asn Pro Asp Phe Pro Pro Glu Val Glu Glu Gln Asp
                245                 250                 255

Ala Ser Thr Leu Pro Val Ser Cys Ala Trp Glu Ser Gly Met Lys Arg
            260                 265                 270

His Arg Ala Ala Cys Ala Ser Ala Ser Ile Asn Val
        275                 280

```
<210> SEQ ID NO 66
<211> LENGTH: 296
<212> TYPE: PRT
<213> ORGANISM: Artificial Sequence
<220> FEATURE:
<223> OTHER INFORMATION: Synthetic protein

<400> SEQUENCE: 66
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ala Ala Ile Ser Gly Ser Gly Asp Asn Thr Tyr Tyr Ala Asp Ser Val
 50                  55                  60

Lys Gly Arg Phe Thr Ile Ser Arg Asp Asn Ser Glu Asn Thr Val His
 65                  70                  75                  80

Leu Gln Met Ala Gly Leu Arg Ala Glu Asp Thr Ala Leu Tyr Phe Cys
                 85                  90                  95

Ala Lys Asp Gly Pro Ala Val Gly Asn Pro Gly Tyr Phe Asp Phe
            100                 105                 110

Trp Gly Arg Gly Thr Leu Val Thr Val Ser Ser Gly Gly Gly Gly Ser
            115                 120                 125

Gly Gly Gly Gly Ser Gly Gly Gly Ser Asp Ile Val Met Thr Gln
            130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Asn Lys Asp Tyr
                165                 170                 175

Leu Ala Trp Tyr Gln Gln Lys Pro Gly Gln Ser Pro Arg Leu Leu Ile
                180                 185                 190

Pro Trp Ala Ser Thr Arg Glu Ser Gly Val Pro Asp Arg Phe Ser Gly
            195                 200                 205

Ser Gly Ser Gly Thr Asp Phe Thr Leu Thr Ile Asn Arg Leu Gln Ala
            210                 215                 220

Glu Asp Val Ala Val Tyr Tyr Cys Gln His Tyr Tyr Ser Tyr Pro Leu
225                 230                 235                 240

Thr Phe Gly Gln Gly Thr Lys Tyr Pro Tyr Asp Val Pro Asp Tyr Ala
            245                 250                 255

Asn Pro Asp Phe Pro Pro Glu Val Glu Glu Gln Asp Ala Ser Thr Leu
            260                 265                 270

Pro Val Ser Cys Ala Trp Glu Ser Gly Met Lys Arg His Arg Ala Ala
            275                 280                 285

Cys Ala Ser Ala Ser Ile Asn Val
            290                 295

<210> SEQ ID NO 67
<211> LENGTH: 283
<212> TYPE: PRT
<213> ORGANISM: Artificial Sequence
<220> FEATURE:
<223> OTHER INFORMATION: synthetic protein

<400> SEQUENCE: 67

Gln Val Gln Leu Val Gln Ser Gly Gly Gly Val Val His Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ser Met Ser Tyr Asp Gly Asn Asn Lys Tyr Tyr Ala Asp Ser Val
 50                  55                  60

Lys Gly Arg Phe Thr Thr Pro Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Arg Gly Ala Leu Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Glu Ile Val Leu Thr Gln Ser Pro Ser Thr Leu Ser
            130                 135                 140

Ala Ser Ile Gly Asp Arg Val Thr Ile Thr Cys Arg Ala Ser Gln Gly
145                 150                 155                 160

Ile Ser Asn Tyr Leu Ala Trp Tyr Gln Gln Lys Pro Gly Lys Ala Pro
                165                 170                 175

Lys Leu Leu Ile Tyr Ala Ala Ser Thr Leu Gln Ser Gly Val Pro Ser
            180                 185                 190

Arg Phe Ser Gly Ser Gly Ser Gly Thr Glu Phe Thr Leu Thr Ile Ser
            195                 200                 205

Gly Leu Leu Pro Glu Asp Phe Ala Ser Tyr Phe Cys Gln Gln Ala Ser
            210                 215                 220

Val Phe Pro Val Thr Phe Ala Arg Thr Lys Tyr Pro Tyr Asp Val Pro
225                 230                 235                 240

Asp Tyr Ala Asn Pro Asp Phe Pro Pro Glu Val Glu Glu Gln Asp Ala
                245                 250                 255

Ser Thr Leu Pro Val Ser Cys Ala Trp Glu Ser Gly Met Lys Arg His
            260                 265                 270

Arg Ala Ala Cys Ala Ser Ala Ser Ile Asn Val
            275                 280

<210> SEQ ID NO 68
<211> LENGTH: 284
<212> TYPE: PRT
<213> ORGANISM: Artificial Sequence
<220> FEATURE:
<223> OTHER INFORMATION: synthetic protein

<400> SEQUENCE: 68

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ala Gly Ala Ile Ala Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Glu Ile Cys Val Thr Gln Ser Pro Ser Phe Leu Ser
            130                 135                 140

Ala Ser Val Gly Asp Arg Val Thr Ile Thr Cys Arg Ala Ser His Gly
145                 150                 155                 160

Ile Asn Asn Tyr Leu Ala Trp Tyr Gln Gln Lys Pro Gly Lys Ala Pro
                165                 170                 175

```
Lys Leu Leu Ile Tyr Ala Ala Ser Ser Leu Gln Ser Gly Val Pro Ser
                180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Ala Asn
        210                 215                 220

Ser Phe Pro Leu Thr Phe Gly Gly Gly Thr Lys Tyr Pro Tyr Asp Val
225                 230                 235                 240

Pro Asp Tyr Ala Asn Pro Asp Phe Pro Pro Glu Val Glu Glu Gln Asp
                245                 250                 255

Ala Ser Thr Leu Pro Val Ser Cys Ala Trp Glu Ser Gly Met Lys Arg
                260                 265                 270

His Arg Ala Ala Cys Ala Ser Ala Ser Ile Asn Val
                275                 280

<210> SEQ ID NO 69
<211> LENGTH: 284
<212> TYPE: PRT
<213> ORGANISM: Artificial Sequence
<220> FEATURE:
<223> OTHER INFORMATION: synthetic protein

<400> SEQUENCE: 69

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Ala Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Ala Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ser Thr Leu Ser
    130                 135                 140

Ala Ser Val Gly Glu Arg Val Thr Ile Thr Cys Arg Ala Ser Gln Ser
145                 150                 155                 160

Ile Ser Ser Trp Leu Ala Trp Tyr Gln Gln Lys Pro Gly Lys Ala Pro
                165                 170                 175

Lys Val Leu Ile Tyr Lys Ala Ser Ser Leu Glu Ser Gly Val Pro Ser
                180                 185                 190

Arg Phe Ser Gly Ser Gly Ser Gly Thr Glu Phe Thr Leu Thr Ile Ser
            195                 200                 205

Ser Leu Gln Pro Asp Asp Phe Ala Thr Tyr Tyr Cys Gln Gln Tyr Ser
        210                 215                 220

Thr Tyr Leu Trp Thr Phe Gly Gln Gly Thr Lys Tyr Pro Tyr Asp Val
225                 230                 235                 240

Pro Asp Tyr Ala Asn Pro Asp Phe Pro Pro Glu Val Glu Glu Gln Asp
                245                 250                 255
```

```
Ala Ser Thr Leu Pro Val Ser Cys Ala Trp Glu Ser Gly Met Lys Arg
            260                 265                 270

His Arg Ala Ala Cys Ala Ser Ala Ser Ile Asn Val
            275                 280

<210> SEQ ID NO 70
<211> LENGTH: 284
<212> TYPE: PRT
<213> ORGANISM: Artificial Sequence
<220> FEATURE:
<223> OTHER INFORMATION: synthetic protein

<400> SEQUENCE: 70

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Val Gly Ala Lys Gly Asn Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Glu Ile Val Leu Thr Gln Ser Pro Ser Thr Leu Ser
    130                 135                 140

Ala Ser Val Gly Glu Arg Val Thr Ile Thr Cys Arg Ala Ser Gln Ser
145                 150                 155                 160

Ile Ser Ser Trp Leu Ala Trp Tyr Gln Gln Lys Pro Gly Lys Ala Pro
                165                 170                 175

Lys Val Leu Ile Tyr Lys Ala Ser Ser Leu Glu Ser Gly Val Pro Asp
            180                 185                 190

Arg Phe Ser Gly Ser Gly Ser Gly Thr Glu Phe Thr Leu Thr Ile Ser
        195                 200                 205

Ser Leu Gln Pro Asp Asp Phe Ala Thr Tyr Tyr Cys Gln Gln Tyr Ser
    210                 215                 220

Thr Tyr Leu Trp Thr Phe Gly Gln Gly Thr Lys Tyr Pro Tyr Asp Val
225                 230                 235                 240

Pro Asp Tyr Ala Asn Pro Asp Phe Pro Pro Glu Val Glu Glu Gln Asp
                245                 250                 255

Ala Ser Thr Leu Pro Val Ser Cys Ala Trp Glu Ser Gly Met Lys Arg
            260                 265                 270

His Arg Ala Ala Cys Ala Ser Ala Ser Ile Asn Val
            275                 280

<210> SEQ ID NO 71
<211> LENGTH: 296
<212> TYPE: PRT
<213> ORGANISM: Artificial Sequence
<220> FEATURE:
<223> OTHER INFORMATION: snthetic protein

<400> SEQUENCE: 71
```

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Ser Gly Ser Gly Asp Asn Thr Tyr Tyr Ala Asp Ser Val
50                  55                  60

Lys Gly Arg Phe Thr Ile Ser Arg Asp Asn Ser Glu Asn Thr Val His
65                  70                  75                  80

Leu Gln Met Ala Gly Leu Arg Ala Glu Asp Thr Ala Leu Tyr Phe Cys
                85                  90                  95

Ala Lys Asp Gly Pro Glu Val Gly Asn Pro Gly Gly Tyr Phe Asp Phe
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Ser Asp Ile Val Met Thr Lys
    130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Lys Asn Lys Asp Tyr
                165                 170                 175

Leu Ala Trp Tyr Gln Lys Lys Pro Gly Gln Ser Pro Arg Leu Leu Ile
            180                 185                 190

Ser Trp Ala Ser Thr Arg Glu Ser Gly Val Pro Asp Arg Phe Ser Gly
        195                 200                 205

Ser Gly Ser Gly Thr Asp Phe Thr Leu Thr Ile Asn Arg Leu Gln Ala
    210                 215                 220

Glu Asp Val Ala Val Tyr Tyr Cys Gln His Tyr Tyr Ser Tyr Pro Leu
225                 230                 235                 240

Thr Phe Gly Gln Gly Thr Lys Tyr Pro Tyr Asp Val Pro Asp Tyr Ala
                245                 250                 255

Asn Pro Asp Phe Pro Pro Glu Val Glu Glu Gln Asp Ala Ser Thr Leu
            260                 265                 270

Pro Val Ser Cys Ala Trp Glu Ser Gly Met Lys Arg His Arg Ala Ala
        275                 280                 285

Cys Ala Ser Ala Ser Ile Asn Val
    290                 295

<210> SEQ ID NO 72
<211> LENGTH: 284
<212> TYPE: PRT
<213> ORGANISM: Artificial Sequence
<220> FEATURE:
<223> OTHER INFORMATION: synthetic protein

<400> SEQUENCE: 72

Gln Val Gln Leu Gln Gln Ser Gly Glu Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Val Gly Ala Lys Gly Asn Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Glu Ile Val Leu Thr Gln Ser Pro Ser Thr Leu Ser
            130                 135                 140

Ala Ser Val Gly Glu Arg Val Thr Ile Thr Cys Arg Ala Ser Gln Ser
145                 150                 155                 160

Ile Ser Ser Trp Leu Ala Trp Tyr Gln Gln Lys Pro Gly Lys Ala Pro
                165                 170                 175

Lys Val Leu Ile Tyr Lys Ala Ser Ser Leu Glu Ser Gly Val Pro Ser
            180                 185                 190

Phe Arg Ser Gly Ser Gly Ser Gly Thr Glu Phe Thr Leu Thr Ile Ser
            195                 200                 205

Ser Leu Gln Pro Asp Asp Phe Ala Thr Tyr Tyr Cys Gln Gln Tyr Ser
210                 215                 220

Thr Tyr Leu Trp Thr Phe Gly Gln Gly Thr Lys Tyr Pro Tyr Asp Val
225                 230                 235                 240

Pro Asp Tyr Ala Asn Pro Asp Phe Pro Pro Glu Val Glu Glu Gln Asp
                245                 250                 255

Ala Ser Thr Leu Pro Val Ser Cys Ala Trp Glu Ser Gly Met Lys Arg
            260                 265                 270

His Arg Ala Ala Cys Ala Ser Ala Ser Ile Asn Val
            275                 280

<210> SEQ ID NO 73
<211> LENGTH: 284
<212> TYPE: PRT
<213> ORGANISM: Artificial Sequence
<220> FEATURE:
<223> OTHER INFORMATION: synthetic protein

<400> SEQUENCE: 73

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
            35                  40                  45

Ala Ser Met Ser Tyr Asp Gly Asp Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Arg Gly Ala Leu Asp Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Glu Ile Val Leu Thr Gln Ser Pro Ser Thr Leu Ser
            130                 135                 140
```

-continued

```
Ala Ser Ile Gly Asp Arg Val Thr Ile Thr Cys Arg Ala Ser Gln Gly
145                 150                 155                 160

Ile Ser Asn Tyr Leu Ala Trp Tyr Gln Gln Lys Pro Gly Lys Ala Pro
                165                 170                 175

Lys Leu Leu Ile Tyr Ala Ala Ser Thr Leu Gln Ser Gly Val Pro Ser
            180                 185                 190

Arg Phe Ser Gly Ser Gly Ser Gly Thr Glu Phe Thr Leu Thr Ile Ser
        195                 200                 205

Gly Leu Leu Pro Glu Asp Phe Ala Ser Tyr Phe Cys Leu Gln Ala Ser
        210                 215                 220

Val Phe Pro Val Thr Phe Gly Gly Gly Thr Lys Tyr Pro Tyr Asp Val
225                 230                 235                 240

Pro Asp Tyr Ala Asn Pro Asp Phe Pro Pro Glu Val Glu Glu Gln Asp
                245                 250                 255

Ala Ser Thr Leu Pro Val Ser Cys Ala Trp Glu Ser Gly Met Lys Arg
                260                 265                 270

His Arg Ala Ala Cys Ala Ser Ala Ser Ile Asn Val
                275                 280
```